(12) United States Patent
Kuhn et al.

(10) Patent No.: US 8,623,340 B2
(45) Date of Patent: Jan. 7, 2014

(54) OMEGA-CYCLOHEXYLALKAN-1-OLES AND USE THEREOF AS ANTIMICROBIAL ACTIVES TO COMBAT BODY ODOR

(75) Inventors: Walter Kuhn, Holzminden (DE); Ingo Wöhrle, Dortmund (DE); Erich Dilk, Holzminden (DE); Christian Ewering, Steinfurt (DE); Jörg Mampel, Bensheim (DE); Michael Krohn, Lorsch (DE); Holger Zinke, Heppenheim (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/266,877

(22) PCT Filed: Apr. 28, 2009

(86) PCT No.: PCT/EP2009/055156
§ 371 (c)(1),
(2), (4) Date: Dec. 29, 2011

(87) PCT Pub. No.: WO2009/101216
PCT Pub. Date: Aug. 20, 2009

(65) Prior Publication Data
US 2012/0107258 A1   May 3, 2012

(51) Int. Cl.
*A61K 8/24* (2006.01)
(52) U.S. Cl.
USPC .............................. 424/65; 514/729; 510/106
(58) Field of Classification Search
None
See application file for complete search history.

(56) References Cited

U.S. PATENT DOCUMENTS

| | | | |
|---|---|---|---|
| 3,408,381 A | 10/1968 | Westland | |
| 4,091,090 A | 5/1978 | Sipos | |
| 4,518,615 A | 5/1985 | Cherukuri et al. | |
| 4,522,948 A | 6/1985 | Walker | |
| 5,002,791 A | 3/1991 | Knebl | |
| 5,093,136 A | 3/1992 | Panhorst et al. | |
| 5,266,336 A | 11/1993 | McGrew et al. | |
| 5,458,894 A | 10/1995 | Knebl et al. | |
| 5,601,858 A | 2/1997 | Mansukhani et al. | |
| 6,172,016 B1 * | 1/2001 | Pagano et al. | 510/106 |
| 6,432,441 B1 | 8/2002 | Bealin-Kelly et al. | |
| 6,986,709 B2 | 1/2006 | Hughs-Baird et al. | |
| 6,986,907 B2 | 1/2006 | Phillips et al. | |
| 2006/0089413 A1 | 4/2006 | Schmaus et al. | |
| 2008/0070825 A1 | 3/2008 | Bertram et al. | |

FOREIGN PATENT DOCUMENTS

| | | |
|---|---|---|
| CH | 655932 A5 | 5/1986 |
| DE | 3740186 A1 | 1/1989 |
| DE | 4229707 A1 | 3/1994 |
| DE | 4229737 A1 | 3/1994 |
| DE | 4324219 A1 | 1/1995 |
| EP | 0242325 A2 | 10/1987 |
| EP | 0 258 967 A2 | 3/1988 |
| EP | 799174 A1 | 10/1997 |
| EP | 0908439 A1 | 4/1999 |
| EP | 1157687 A2 | 11/2001 |
| EP | 1269983 A1 | 1/2003 |
| EP | 2014273 A1 | 1/2009 |
| WO | WO-9619428 A1 | 6/1996 |
| WO | WO-0143784 A2 | 6/2001 |
| WO | WO-0176572 A2 | 10/2001 |
| WO | WO-0215868 A2 | 2/2002 |
| WO | WO-0241861 A1 | 5/2002 |
| WO | WO-03024907 A1 | 3/2003 |
| WO | WO-2004050069 A1 | 6/2004 |
| WO | WO-2005004601 A1 | 1/2005 |
| WO | WO-2005107692 A1 | 11/2005 |
| WO | WO-2005123101 A1 | 12/2005 |
| WO | WO-2006015954 A1 | 2/2006 |
| WO | WO-2006032668 A1 | 3/2006 |
| WO | WO-2006045760 A1 | 5/2006 |
| WO | WO-2006053912 A1 | 5/2006 |
| WO | WO-2006124230 A1 | 11/2006 |
| WO | WO-2007042472 A1 | 4/2007 |
| WO | WO-2007110415 A2 | 10/2007 |
| WO | WO-2008046676 A1 | 4/2008 |
| WO | WO-2008046791 A1 | 4/2008 |
| WO | WO-2008046795 A1 | 4/2008 |
| WO | WO-2008119841 A2 | 10/2008 |

\* cited by examiner

*Primary Examiner* — Janet Epps-Smith
*Assistant Examiner* — Yanzhi Zhang
(74) *Attorney, Agent, or Firm* — Novak Druce Connolly Bove + Quigg LLP

(57) ABSTRACT

The present invention relates to antimicrobially active ω-cyclohexylalkan-1-oles of the following formula (I), to a method for producing said compounds and to the use thereof as antimicrobial agents for treating body odor,

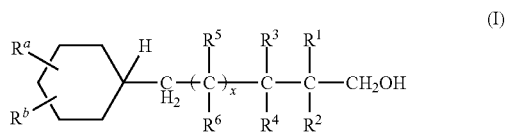

(I)

wherein $R^1$ to $R^6$ independently of one another denote hydrogen or a linear or branched alkyl radical having 1 to 12 carbon atoms, $R^a$ and $R^b$ independently of one another denote hydrogen, a linear or branched alkyl radical having 1 to 6 carbon atoms or a linear or branched alkoxy radical having 1 to 4 carbon atoms, and x is 0 or 1, wherein preferably the total number of carbon atoms in $R^1$ to $R^6$ is 18 or less.

14 Claims, No Drawings

OMEGA-CYCLOHEXYLALKAN-1-OLES AND USE THEREOF AS ANTIMICROBIAL ACTIVES TO COMBAT BODY ODOR

CROSS-REFERENCE TO RELATED APPLICATIONS

This application is a National Phase filing under 35 U.S.C. §371 of PCT/EP2009/055156, filed Apr. 28, 2009, the entire contents of which is incorporated herein by reference.

The present invention relates to antimicrobially active ω-cyclohexylalkan-1-oles of the following formula (I), to a method for producing said compounds and to the use thereof as antimicrobial agents for treating body odor,

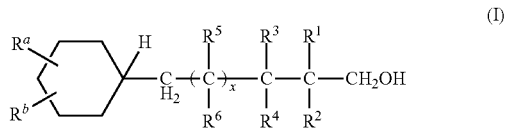

wherein
$R^1$ to $R^6$ independently of one another denote hydrogen or a linear or branched alkyl radical having 1 to 12 carbon atoms, $R^a$ and $R^b$ independently of one another denote hydrogen, a linear or branched alkyl radical having 1 to 6 carbon atoms or a linear or branched alkoxy radical having 1 to 4 carbon atoms, and
x is 0 or 1,
wherein preferably the total number of carbon atoms in $R^1$ to $R^8$ is 18 or less, more preferably the total number of carbon atoms in $R^1$ to $R^6$ is 1 to 12.

In this context, the substituents $R^a$ and $R^b$ can in each case occupy (as indicated by the drawing) any desired position on the cyclohexyl ring (ortho, meta or para to the alkan-1-ole radical).

The compounds of formula (I) are outstandingly suitable as antimicrobial active ingredients for the cosmetic, in general for the dermatological, treatment of microorganisms which cause body odor.

Human skin is colonized by numerous different bacteria. Most of these bacteria are non-pathogenic and of no relevance to the physiological condition of the skin and to its odor. Others, in contrast, can have a major influence on the healthy condition of the skin. Table 1 lists some microorganisms which have a strong influence on human body odor.

TABLE 1

| Microorganisms: | |
| --- | --- |
| *Staphylococcus epidermidis* | Underarm odor; body odor in general |
| *Corynebacterium xerosis* | Underarm odor |
| *Brevibacterium epidermidis* | Underarm odor; foot odor |

Bacterial degradation of endogenous substances present in perspiration, such as for example unsaturated fatty acids, gives rise from precursors, which to a greater or lesser extent have a slight odor, to unpleasant smelling decomposition products which can have a major impact on physical well-being. Formation of the substances responsible for body odor is prevented in cosmetic applications either by using products which suppress the formation of sweat ("antiperspirants") or by using substances which inhibit the growth of human skin bacteria responsible for odor formation ("deodorants"). Species of bacteria such as *Staphylococcus epidermidis*, *Corynebacterium xerosis* and *Brevibacterium epidermidis* are largely responsible for the formation of underarm and foot odor, or body odor in general. There is accordingly a constant need in the cosmetics industry for new agents for treating these microorganisms and others which cause body odor (including underarm and foot odor).

The compounds of formula (I) according to the invention have in our trials demonstrated that in combination with a variety of fragrance odor types they are capable of generating a sense of hygiene and/or cleanliness not only in the user but also in third parties. They proved to be effective against body odor, and more specifically the smell of human sweat, especially the smell of underarm sweat.

In the context of this text a sense of hygiene and/or cleanliness means a perception by humans via the nasal cavity, in particular via the sense of smell, which is associated with hygiene/cleanliness.

Body odor, in particular body odor from pathological sweating (hyperhydrosis) and including foot odor, can have considerable, including psychological, effects on the individual concerned. Therefore the application according to the invention is also suited to use in the area of medicine, in particular for the prevention, reduction or treatment of the psychological effects of body odor, in particular pathological body odor.

For the purposes of the present document, "treatment" or antimicrobial activity should be taken to mean exerting any kind influence on the microorganisms in question, in which multiplication of these microorganisms is inhibited and/or the microorganisms are killed.

In seeking out such antimicrobially active agents, it must be borne in mind that the substances used in cosmetic and/or pharmaceutical products must furthermore
- be toxicologically safe,
- exhibit good skin compatibility,
- be stable (in particular in conventional cosmetic and/or pharmaceutical formulations),
- preferably have only a slight odor or be (largely) odorless,
- preferably be colorless and cause no discoloration, and
- be inexpensive to produce (i.e. using standard methods and/or starting from standard precursors).

The search for suitable (antimicrobially active or otherwise affecting the generation of body odor) substances which exhibit one or more of the stated characteristics to a sufficient extent is complicated for a person skilled in the art by the fact that there is no clear dependency between the chemical structure of a substance, on the one hand, and its biological activity towards specific microorganisms (microbes) and their stability, on the other hand. Moreover, there is no predictable connection between antimicrobial action, toxicological safety, skin compatibility and/or stability.

it was accordingly the object of the present invention to provide an antimicrobial active ingredient which is active in particular against microorganisms such as *Corynebacterium xerosis*, *Staphylococcus epidermidis* and *Brevibacterium epidermidis*, which cause body odor and foot odor, and which in so doing preferably also satisfies one or more of the above-stated secondary conditions.

EP 1 157 687 describes antimicrobial deo formulations containing certain phenyl substituted alcohols like phenoxyethanol, anise alcohol or 2-methyl-5-phenylpentanol as antimicrobial active substances.

EP 0 799 174 A1 describes ω-phenylalkan-1-oles as biocidal active ingredients.

We now have surprisingly found that the novel compounds of formula (I) according to the present invention of the formula (I) have excellent antimicrobial properties and in particular are active against the stated microorganisms. Further investigations into their chemical properties revealed that the compounds are highly stable, in particular by elevated temperature stability and by high stability over a wide range of pH values, as a consequence of which it is ideally suitable for use in the most varied range of cosmetic products (cosmetic formulations) and pharmaceutical products. In addition, in pure form, the compounds according to the invention of the formula (I) form colorless solutions in (cosmetic and/or pharmaceutical) carriers; furthermore, no discoloration was observed after incorporation of the compounds according to the invention of the formula (I) in cosmetic products and in pharmaceutical preparations.

Preferred compounds of formula (I) are those in which x is 1 (i.e. cyclohexylpentan-1-oles), because these compounds showed improved activity against body odor causing microorganisms.

Further preferred compounds of formula (I) are those in which $R^a$ is hydrogen and $R^b$ is hydrogen or is in 4- (i.e. para) position and denotes a linear or branched alkyl radical having 1 to 6 carbon atoms.

Further preferred compounds of formula (I) correspond to the following formula (II)

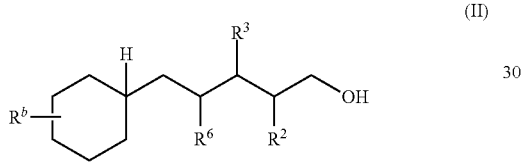

(II)

wherein
$R^2$, $R^3$ and $R^6$ independently of one another denote hydrogen or a linear or branched alkyl radical having 1 to 8 carbon atoms,
$R^b$ denotes hydrogen, a linear or branched alkyl radical having 1 to 4 carbon atoms or a linear or branched alkoxy radical having 1 to 4 carbon atoms, and
wherein the total number of carbon atoms in $R^2$, $R^3$ and $R^6$ is 1 to 8, and wherein preferably $R^b$ is in para position.

Further preferred compounds of formula (I) correspond to the following formula (III)

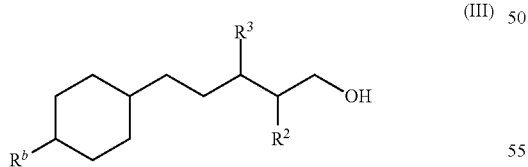

(III)

wherein
$R^2$ and $R^3$ independently of one another denote hydrogen or a linear or branched alkyl radical having 1 to 6 carbon atoms,
$R^b$ denotes hydrogen, methyl, ethyl, propyl, isopropyl, tert.-butyl, methoxy or isopropoxy, and
wherein the total number of carbon atoms in $R^2$, $R^3$ and $R^6$ is 1 to 12.

Individual more preferred compounds according to the present invention are:

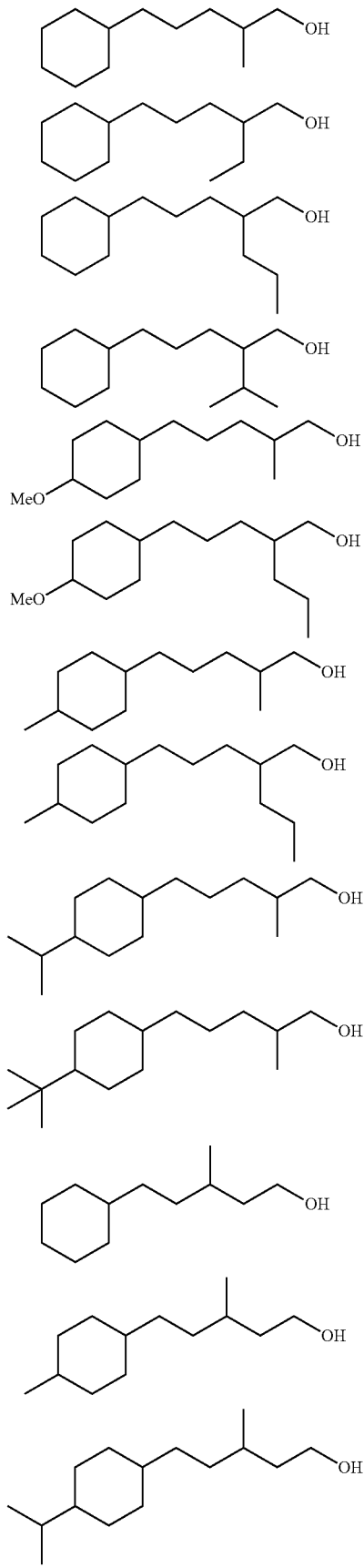

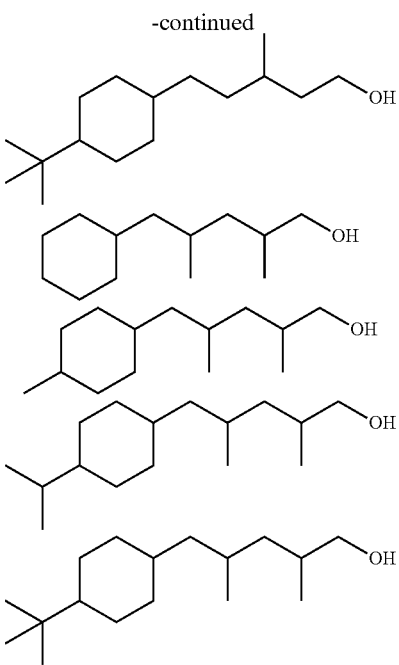

Even more preferred compounds of formula (I) correspond to the following formula (IV)

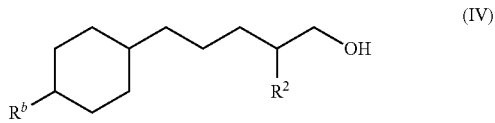

(IV)

wherein
$R^2$ denotes a linear or branched alkyl radical having 1 to 6 carbon atoms, and
$R^b$ denotes hydrogen, methyl, ethyl, propyl, isopropyl or tert.-butyl.

Most preferably in formula (IV) $R^b$ denotes hydrogen and/or $R^2$ denotes a linear or branched alkyl radical having 1 to 3 carbon atoms. In particular, preferred substances are:

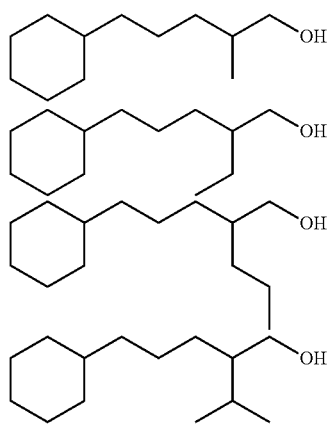

A method for producing the compounds of the formula (I) and the use thereof as antimicrobially active ingredients in cosmetic products and in pharmaceutical preparations are likewise described herein.

The compounds of formula (I) have a strong antimicrobial action towards odor-forming microorganisms on human skin and may thus ideally be used as a deodorant as an alternative or supplement to known antimicrobial active ingredients (such as for example farnesol) in cosmetic products, in pharmaceutical products and the like.

In particular, the compounds of formula (I) according to the invention or a (preferably cosmetic) product according to the invention is capable of inhibiting and/or preventing the growth of microorganisms which cause body odor, and/or of killing these, which are chosen from the group consisting of: *Staphylococcus, Corynebacterium* and *Brevibacterium* species, in particular *Staphylococcus epidermidis, Corynebacterium xerosis* and *Brevibacterium epidermidis*.

The compounds of formula (I) according to the invention or a (preferably cosmetic) product according to the invention are distinguished in particular by a very good action against gram-positive bacteria.

In a preferred method for cosmetic and/or therapeutic treatment of microorganisms which cause body odor, an antimicrobially active amount of one or more compounds according to the invention of the formula (I) is applied topically onto the human body, such that growth of the microorganism(s) which are possibly present is inhibited and/or the microorganism(s) are killed.

It was further found that the compounds of formula (I) according to the invention are able to inhibit and/or prevent the growth of biofilms and/or to reduce a biofilm already present, in particular biofilms stemming from or involving microorganisms from the group consisting of: *Staphylococcus, Corynebacterium* and *Brevibacterium* species, in particular *Staphylococcus epidermidis, Corynebacterium xerosis* and *Brevibacterium epidermidis*.

The compounds of formula (I) are also particularly suitable for either inhibition of initial biofilm formation, stagnation or even detachment of a pre-existing biofilm. These findings are inter alia based on a series of investigations relating to the particularly relevant microorganism *Corynebacterium xerosis* in the context of the present invention, as described in the Examples in more detail.

A biofilm is a structured community of microorganisms encapsulated within a self-developed polymeric matrix and adherent to a living or inert surface. Biofilms are also often characterized by surface attachment, structural heterogeneity, genetic diversity, complex community interactions, and an extracellular matrix of polymeric substances.

Formation of a biofilm begins with the attachment of free-floating microorganisms to a surface. These first colonists adhere to the surface initially through weak, reversible van der Waals forces. If the colonists are not immediately separated from the surface, they can anchor themselves more permanently using cell adhesion structures. The first colonists facilitate the arrival of other cells by providing more diverse adhesion sites and beginning to build a matrix that holds the biofilm together. Some species are not able to attach to a surface on their own but are often able to anchor themselves to the matrix or directly to earlier colonists. Once colonization has begun, the biofilm grows through a combination of cell division and recruitment. The final stage of biofilm formation is known as development, and is the stage in which the biofilm is established and may only change in shape and size. This development of biofilm allows for the cells to become more antibiotically resistant.

The biofilm is held together and protected by a matrix of excreted polymeric compounds called EPS. EPS is an abbreviation for either extracellular polymeric substance or exopolysaccharide. This matrix protects the cells within it and facilitates communication among them through biochemical signals. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community.

Biofilms are usually found on solid substrates exposed to aqueous solutions or in areas of high humidity. Given sufficient resources for growth, a biofilm can quickly grow to be macroscopic. Biofilms can contain many different types of microorganism, e.g. bacteria, archaea, protozoa, fungi and algae; each group may be performing specialized metabolic functions. However, some organisms will form monospecies films under certain conditions.

Thus, an "antimicrobially effective amount" of the substances of formula (I) of the present invention signifies an amount suitable for
(a) killing any of the aforementioned microorganisms *C. xerosis, S. epidermidis* and/or *B. epidermidis*,
(b) inhibit or reduce their growth rate,
(c) inhibit or alter their metabolism to prevent or reduce conversion of precursors to unpleasently smelling decomposition products, and/or
(d) inhibit or prevent the growth of a biofilm or reduce a biofilm.

The compounds according to the invention of the formula (I) may be obtained by a production method which comprises the following step:
reduction, preferably hydrogenation, of a ω-phenylalkan-1-ole of formula (S)

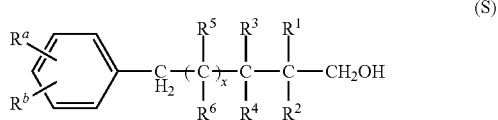

wherein $R^1$ to $R^6$, $R^a$, $R^b$ and x have the corresponding (preferred) meaning given above.

The ω-phenylalkan-1-oles of formula (S) used as starting material for producing the compounds of formula (I) can be obtained in accordance with or similar to the processes described in the prior art. Reference is made to WO 96/19428, CH 655 932 and EP 0 908 439. Some of the starting materials are also commercially available, e.g. 2-methyl-5-phenylpentanol (e.g. Rosaphen™ from Symrise) or 3-methyl-5-phenylpentanol (e.g. Phenoxanol™ from IFF).

According to the invention, the hydrogenation of ω-phenylalkan-1-oles of formula (S) preferably is carried out in the presence of a hydrogenation catalyst. The hydrogenation catalysts according to the invention preferably comprise at least one metal from subgroup 8 in elemental, metallic form.

These metals can, for example, be used in finely divided form, applied to supports or together with other metals (e.g. mixtures, alloys). The catalysts can comprise dopings with one or more further metals.

Suitable catalysts can comprise, preferably in metallic form, for example: ruthenium, rhodium, iridium, nickel, palladium and/or platinum. Preferred catalysts for the purposes of the hydrogenation process of the compounds of formula (S) comprise palladium, platinum, ruthenium or rhodium, preferably in metallic form.

The metals according to the invention can be applied to organic or inorganic support materials. The catalysts can comprise a support material or mixtures of support materials. Advantageous support materials are: activated carbon, carbon, metal oxides, aluminium oxides, silica gels, zeolites, clays, clay granules, amorphous aluminium silicates and other inorganic supports. Preferred support materials are activated carbon and aluminium oxide.

A particularly preferred hydrogenation catalyst is ruthenium on activated carbon or on aluminium oxide.

If catalysts comprising support materials are used, the proportion of catalyst metal on the support material may generally be 0.5 to 50% by weight, preferably 1 to 20% by weight, particularly preferably 3 to 10% by weight, based on the total dry catalyst.

For the process according to the invention, the catalyst can be used in the dry or moist state (residual moisture of water).

The hydrogenation process can be carried out continuously, semicontinuously and batchwise.

The hydrogenation process of the compounds of formula (S) according to the invention can be carried out using solvents or solvent mixtures. Suitable are, for example, alcohols, aqueous alcohols, ethers, esters, aromatic or saturated hydrocarbons. For example, solvents such as methanol, ethanol, isopropanol, n-propanol, isobutanol, n-butanol, sec-butanol, tetrahydrofuran, dibutyl ether, ethylene glycol dimethyl ether, ethyl acetate, methyl acetate, pentane, hexane, heptane, octane, cyclopentane, cyclohexane, methylcyclohexane, cyclooctane, can be used. In one preferred embodiment the hydrogenation process is carried out in absence of a solvent.

The hydrogenation process of the compounds of formula (S) can preferably be carried out at temperatures in the range from 50 to 220° C., preferably in the range from 70 to 160° C., particularly preferably at 80 to 130° C.

According to the invention, the hydrogenations are carried out with elemental hydrogen. The hydrogen pressure is suitably 1 to 100 bar, preferably 10 to 30 bar.

The reaction time of the hydrogenation of the compounds of formula (S) is preferably 1 to 100 hours, particularly preferably 10 to 50 hours, particularly preferably 20 to 40 hours.

Further aspects of the present invention are also disclosed by the attached claims and the following examples. Unless otherwise stated, all stated values relate to weight.

Compositions and products, in particular (topical) cosmetic products, according to the present invention can advantageously comprise (apart from the one or more compounds of formula (I) according to the invention) suitable auxiliary substances and additives, such as, for example:
preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, anti-cellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

Deodorants and antiperspirants (antiaspirants) are cosmetic preparations which are used for prevention and removal of unpleasant body odor, in particular the smell of underarm (axillary) sweat. They provide the user with the sense of improved hygiene and cleanliness. The sense of hygiene and cleanliness is here generally triggered by stimuli in the nasal cavity. Such a sense also occurs in particular if pleasant smells are perceived generally or reinforced, or unpleasant smells, in particular those associated with lack of (personal) hygiene, such as the smell of sweat, are not or are no longer perceived.

The way in which deodorants and antiperspirants work can be based on a variety of mechanisms. Thus various active substances can be used, such as
  substances with a deodorizing effect (deodorants):
    antimicrobially acting substances, enzyme inhibiting substances, odor absorbing substances, odor neutralizing substances and odor masking substances; and
  sweat-inhibiting substances (antiperspirants, antitranspirants).

The effect of these substances is predominantly intended, over as long a period as possible, to prevent the development of unpleasant body odor or the perception of such odor.

"Olfactory" in this connection means the sensations perceived via the nasal cavity, in particular via the sense of smell.

The compounds according to the invention of formula (I) may also be used as a constituent of fragrance compositions (perfume oils) and, for example, impart an antimicrobial action to a perfumed finished product. It has proved particularly advantageous that the cyclohexyl derivatives of formula (I) according to the present invention have a weak intrinsic flowery/blossom odor which generally was observed to be weaker in intensity and impact compared to the odor of the corresponding phenyl compounds (see formula (S) as described above); this characteristic makes the compounds of the present invention ideally suitable for use as a deodorizing active ingredient in a fragrance composition or a perfumed (cosmetic) product, because the odor impression of the said fragrance composition or a perfumed (cosmetic) product is not substantially changed or adulterated by including the compounds according to the invention of formula (I) into said compositions or products.

The compounds according to the invention of formula (I) do not adversely affect other substances, typically those contained in cosmetic preparations. This is In particular of relevance in connection with the herein preferred (cosmetic) products, in particular deodorants or antiperspirants.

Fragrance compositions (perfume oils) in the context of the present invention relate to mixtures of two or more odoriferous substances (fragrance materials), preferably to three, four, five, six, seven, eight, nine, ten or more odoriferous substances (fragrance materials).

Thus, an important advantage of the perfume oils according to the invention is that the compounds of formula (I) according to the invention, because of their very weak inherent odor, only slightly contribute to the overall odor impression of the fragrance composition, thereby not adulterating said overall odor impression.

Like the perfume oils according to the invention, the (topical) cosmetic or pharmaceutical preparations according to the invention have the advantage that because of the comparatively weak inherent smell of the compounds of formula (I) according to the invention the cosmetic preparations according to the invention are not associated with specific odor types and thus as regards their actual composition are restricted only very slightly, by the compounds according to the invention.

A particularly preferred fragrance composition comprises
(a) an antimicrobially active amount of one or more compounds of formula (I),
(b) an organoleptically active amount of a fragrance (two or more odoriferous substances), and
(c) optionally one or more carriers and/or additives acceptable for perfumery.

Preferred fragrance compositions according to the invention include as carriers acceptable for perfumery one or more carriers from the group consisting of dipropylene glycol (DPG), diethyl phthalate (DEP), triethyl citrate (TEC), isopropyl myristate (IPM), and/or benzyl benzoate (BB).

A particularly preferred perfumed cosmetic product or formulation comprises
(a) an antimicrobially active amount of one or more compounds of formula (I),
(b) an organoleptically active amount of a fragrance (two or more odoriferous substances), and
(c) one or more cosmetically acceptable carriers and/or cosmetic additives.

Preferred cosmetic formulations according to the invention include an antimicrobially active amount of one or more compounds of the formula (I) and a perfume oil in a total quantity in the range of 0.1 to 3% by weight, preferably in the range of 0.2 to 2% by weight, with particular preference for a range of 0.3 to 1.5% by weight, with reference to the total mass of the cosmetic preparation.

In a preferred fragrance composition or a preferred perfumed (cosmetic) product or formulation according to the present invention the ratio by weight of the total amount of fragrances to the total amount of compounds of formula (I) is in the range of 25:1 to 1:10, preferably in the range of 15:1 to 1:5, more preferably in the range of 10:1 to 1:3, most preferably in the range of 5:1 to 1:2.

The invention also relates to antimicrobial compositions which, in addition to (a) an antimicrobially active amount of the one or more compounds according to the invention of formula (I), also comprise (b) a carrier substance compatible with component (a).

The total usage concentration of the compounds of formula (I) according to the present invention in a (preferably topical) final (cosmetic) product preferably is in the range of from 0.01 to 10 wt. %, preferably in the range of from 0.05 to 5 wt. %, particularly preferably in the range of from 0.1 to 2.5 wt. %, and most preferably in the range of from 0.2 and 0.8 wt. %, in each case relative to the total mass of the (cosmetic) product, in particular deodorants and antiperspirants.

Because of their comparatively neutral odor profile the compounds of formula (I) of the invention can be combined exceptionally well, and easily blended, with fragrances to form various types of scent and thus perfume oils according to the invention without this resulting in a problematical alteration to the sensorial characteristics of said fragrances. Such scent compositions preferably comprise two, three, four, five, six, seven, eight, nine, ten or more of the (preferred) fragrances mentioned below.

Where perfume oils or preparations according to the invention contain, in addition to a compound of formula (I) according to the invention, natural fragrance materials, in particular essential oils, concretes, absolutes, resins, resinoids, balsams and/or tinctures, these are preferably selected from the group consisting of:
ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; bade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineol type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil.

Individual fragrance materials are preferably selected from the group comprising:
hydrocarbons, such as for example 3-carene; α-pinene; β-pinene; α-terpinene; γ-terpinene; p-cymene; bisabolene; camphene; caryophyllene; cedrene; farnesene; limonen; longifolene; myrcene; ocimene; valencene; (E,Z)-1,3,5-undecatriene; styrene; diphenylmethane;
aliphatic alcohols, such as for example hexanol; octanol; 3-octanol; 2,6-dimethylheptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-al; 9-decenol; 10-undecenol; 4-methyl-3-decen-5-ol;
aliphatic aldehydes and their acetals such as for example hexanol; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyace-aldehyde; 1-(1-methoxy-propoxy)-(E/Z)-3-hexene;
aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one;
aliphatic sulphur-containing compounds, such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;
aliphatic nitriles, such as for example 2-nonenenitrile; 2-undecenenitrile; 2-tridecenenitrile; 3,12-tridecenenitrile; 3,7-dimethyl-2,6-octadienenitrile; 3,7-dimethyl-6-octenenitrile;
aliphatic carboxylic acids esters, such as for example (E)- and (Z)-3-hexenylformate; ethyl acetoacetate; isoamyl acetate;

hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate; 4-Methyl-2-pentylcrotonate;

acyclic terpene alcohols, such as, for example, citronellol; geraniol; nerol; linalool; lavandulol; nerolidol; farnesol; tetrahydrolinaloot; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl- and diethylacetals of geranial, neral and 7-hydroxy-3,7-dimethyloctanal;

cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; paid; and the formates, acetates, propionates, isobutyrates, butyrates, isovalerates, pentanoates, hexanoates, crotonates, tiglinates and 3-methyl-2-butenoates thereof; menthyl formiate; menthyl propionate; methyl butyrate; methyl losbutyrate, methyl isovalerate, menthyl hexanoate; menthly crotonate, manethyl tiglinate;

cyclic terpene aldehydes and ketones, such as, for example, menthone; isomenthone; 8-mercaptomenthan-3-one; carvone; camphor; fenchone; alpha-ionone; beta-ionone; beta-n-methyl ionone; beta-isomethyl ionone; alpha-irone; alpha-damascone; beta-damasoone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (cedryl methyl ketone);

cyclic alcohols, such as, for example, 4-tert.-butylcyclohexanol; 3,3,5-trimethylcyclohexanol; 3-isocamphylcyclohexanol; 2,6,9-trimethyl-Z2, Z5, E9-cyclododecatrien-1-ol; 2-isobutyl-4-methyltetrahydro-2H-pyran-4-ol;

cycloaliphatic alcohols, such as, for example, alpha,3,3-trimethylcyclo-hexylmethanol; 1-(4-isopropylcyclohexyl) ethanol; 2-methyl-4-(2,2,3-trimethyl-3-cyclopent-1-yl) butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl) hexan-3-ol;

cyclic and cycloaliphatic ethers, such as, for example, cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyl-dodecahydronaphtho [2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxan;

cyclic and macrocyclic ketones, such as, for example, 4-tert.-butylcyclohexanone; 2,2,5-trimethyl-5-pentylcyclopentanone; 2-heptylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl) ketone;

esters of cyclic alcohols, such as, for example, 2-tert.-butyl-cyclohexyl acetate; 4-tert.-butylcyclohexyl acetate; 2-tert.-pentylcyclohexyl acetate; 4-tert.-pentylcyclohexyl acetate; 3,3,5-trimethylcyclohexyl acetate; decahydro-2-naphthyl acetate; 2-cyclopentylcyclopentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl-isobutyrate; 4,7-methanooctahydro-5 or 6-indenyl acetate;

esters of cycloaliphatic alcohols, such as, for example, 1-cyclohexylethylcrotonate;

esters of cycloaliphatic carboxylic acids, such as, for example, allyl 3-cyclohexyl-propionate; allyl cyclohexyl oxyacetate; cis- and transmethyl dihydrojasmonate; cis and transmethyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxotane-2-acetate;

aralphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenyl propanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 3-methyl-5-phenylpentanol; 3-phenyl-2-propen-1-ol; 4-methoxybenzyl alcohol; 1-(4-isopropylphenyl)ethanol;

esters of aralphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha, alpha-dimethylphenylethyl acetate; alpha, alpha-dimethylphenylethyl butyrate; cinnamyl acetate; 2-phenoxyethyl isobutyrate; 4-methoxybenzyl acetate;

aralphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno [1,2-d]m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl) propanal; 2-methyl-3-(4-tert.-butylphenyl) propanal; 2-methyl-3-(4-isobutylphenyl) propanol; 3-(4-tert.-butylphenyl) propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl) propanal; 2-methyl-3-(4-methylendioxyphenyl)propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexa-methyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methyl-N-methylanthranilate;

Schiffs bases of methyl anthranilate with 7-hydroxy-3,7-dimethyloctanal, 2-methyl-3-(4-tert.-butylphenyl) propanal or 2,4-dimethyl-3-cyclohexene carbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine;

phenols, phenyl ethers and phenyl esters, such as, for example, estragole; anethole; eugenol; eugenyl methyl ether; isoeugenyl; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,13-tridecanedioate; coumarin; 2,3-dihydrocoumarin; octahydrocoumarin.

It has also been discovered that perfume oils according to the invention comprising (i) one or more compounds of formula (I) according to the invention and (ii) one or more of the fragrances of group (B) lead to an overall improvement in the sense of hygiene and cleanliness with improved body odor reducing, neutralising or masking effect.

In a further preferred embodiment the one or more compounds of formula (I) according to the invention are combined with, preferably, two, three, four, five or more of the fragrance materials from group (B) mentioned below, since such combinations can give a particularly distinct sense of hygiene and cleanliness, wherein they demonstrate an improved body odor reducing, neutralizing or odor masking effect.

Group (B) of fragrance materials consists of: (here in some cases the normal industrial product names and registered trademarks of various firms are given) alpha-hexylcinnamaldehyde, 2-phenoxyethylisobutyrate (Phenirat), dihydromyrcenol (2,6-dimethyl-7-octen-2-ol), methyl dihydrojasmonate; preferably with a content of cis-isomers of >60 by weight (Hedione, Hedione HC), 4,6,6,7,8,8-hexamethyl-1,3,4,6,7,8-hexahydrocyclopenta[g]benzopyran (Galaxolid), tetrahydrolinalool (3,7-dimethyloctan-3-ol), ethyllinalool, benzylsalicylate, 2-methyl-3-(4-tert-butylphenyl)propanal (Lilial), cinnamon alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat), citronellol, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethyl-naphthaline (Iso E Super), hexylsalicylate, 4-tert.-butylcyclohexyl acetate (Oryclon), 2-tert.-butylcyclohexyl acetate (Agrumex HC), alpha-ionone (4-(2,2,6-trimethyl-2-cyclohexen-1-yl)-3-buten-2-one), coumarin, terpinyl acetate, 4-(4-hydroxy-4-methylpentyl)-3-cyclohexene carboxaldehyde (Lyral), alpha-amyl cinnamon aldehyde, (E)- and/or (Z)-3-methylcyclopentadec-5-enone (Muscenon), 15-pentadec-11-enolide and/or 15-pentadec-12-enolide (Globelide), 15-cyclopentadecanolide (Macrolide), 1-(5,6,7,8-tetrahydro-3,5,5,6,8,8-hexamethyl-2-naphthalenyl)ethanone (Tonalid), 2-isobutyl-4-methyltetrahydro-2H-pyran-4-ol (Florol), 2-ethyl-4-(2,2,3-trimethyl-3-cyclopenten-1-yl)-2-buten-1-ol (Sandolen), menthol (preferably l-menthol or racemic menthol, with particular preference for l-menthol), anethole, geraniol, nerol, linalool, citronellol, linalyi acetate, 2-phenylethyl alcohol, 2,2-dimethyl-3-(3-methylphenyl)-propanol (Majantol), rose oxide (4-methyl-2-(2-methyl-1-propenyl) tetrahydropyran), allyl heptanoate, 4-methylacetophenone, (4aR,5R,7aS,9R)-octahydro-2,2,5,8,8,9a-hexamethyl-4H-4a,9-methanoazuleno(5,6-d)-1,3-dioxol) (Ambrocenide), Timberol (1-(2,2,6-trimethylcyclohexyl)hexan-3-ol), Floropal (2,4,6-trimethyl-4-phenyl-1,3-dioxan), benzylacetone, methyl cinnamate, 3a,6,6,9a-tetramethyldodecahydronaphtho[2,1-b]furan (Ambroxid).

In perfume oils and cosmetic preparations according to the invention, in particular deodorants and antiperspirants, the weight ratio of the total quantity of the fragrance materials from group (B) to the total quantity of the compounds of formula (I) according to the invention is preferably in the range of 20:1 to 1:12.5, preferably in the range of 12:1 to 1:6.25, more preferably in the range of 8:1 to 1:3.75, most preferably in the range of 4:1 to 1:2.5.

Individual preferred cooling agents for use in connection with the present invention (in perfume oils or preparations according to the invention) are listed in the following. The listed cooling agents can also be used in combination with each other here: menthone glycerine acetal (trade name: Frescolat®MGA), menthyl lactate (trade name: Frescolat®ML, this is preferably for menthyl lactate a case of 1-menthyl lactate, in particular l-menthyl-l-lactate), substituted menthyl-3-carboxylic acid amide (e.g. menthyl-3-carboxylic acid-N-ethylamide), 2-isopropyl-N-2,3-trimethylbutanamide, substituted cyclohexane carboxylic acid amide, 3-menthoxypropane-1,2-diol, 2-hydroxyethylmenthylcarbonate, 2-hydroxypropylmenthylcarbonate, N-acetyl glycine menthyl ester, Isopulegol, menthyl hydroxycarboxylic acid ester (e.g. menthyl-3-hydroxybutyrate), monomenthylsuccinate, 2-mercaptocyclodecanone, menthyl-2-pyrrolidin-5-one carboxylate, 2,3-dihydroxy-p-menthane, 3,3,5-trimethyl cyclohexanone glycerine ketal, 3-menthyl-3,6-di- and -trioxalkanoate, 3-menthylmethoxy acetate, Icilin.

Preferred cooling agents are: menthone glycerine acetal (trade name: Frescolat®MGA), menthyl lactate (preferably l-menthyl lactate, in particular l-menthyl-l-lactate, trade name: Frescolat®ML), 3-menthoxy propane-1,2-diol, 2-hydroxyethyl menthyl carbonate, 2-hydroxypropyl menthyl carbonate, particular preference being for 1-menthyl-l-lactate.

Also preferred are (topical) cosmetic or pharmaceutical compositions/products according to the present invention comprising one or more actives selected from the groups consisting of:
(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone; and/or
(ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone; and/or
(iii) natural or naturally occurring anti-inflammatory substances or substances that alleviate reddening and/or itching, in particular extracts or fractions from camomile, *Aloe vera*, *Commiphora* species, *Rubia* species, willow, willow-herb, oats, calendula, arnica, St John's wort, honeysuckle, rosemary, *Passiflora incarnata*, witch hazel, ginger or Echinacea, and/or
(iv) pure substances, preferably alpha-bisabolol, apigenin, apigenin-7-glucoside, gingerols, shogaols, gingerdiols, dehydrogingerdiones, paradols, natural avenanthramides, non-natural avenanthramides, preferably dihydroavenanthramide D, boswellic acid, phytosterols, giycyrrhizin, glabridin and licochalcone A; and/or
(v) skin care agents, preferably skin moisture retention regulators or skin repair agents, preferably selected from the group consisting of sodium lactate, urea and derivatives, glycerol, propylene glycol, 1,2-pentanediol, 1,2-hexanediol and 1,2-octanediol, collagen, elastin or hyaluronic acid, diacyl adipates, petrolatum, urocanic acid, lecithin, allantoin, panthenol, phytantriol, lycopene, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts.

The compounds of formula (I) and perfume oils according to the invention can be included in all products, in particular (deo-)preparations (deodorants), which are suitable for reducing body odor, in particular the unpleasant smell of sweat, with products that remain on the skin or hair (so-called leave-on products) being particularly advantageous, i.e. products which are applied to the human skin or hair an remaining on said skin or hair, preferably for at least 10 minutes, more preferably for at least 30 minutes.

The form of administration of the leave-on products can vary greatly and may include sprays, gels, foams, balms, tinctures, lotions, crémes, milks, oils and sticks. The following products can be cited as examples: deodorants (e.g. pump sprays, atomizers, propellant aerosol sprays, roll-ons, gels, cremes, sticks, foams); air fresheners (e.g. gels or liquids); body lotions, body cremes or body milks (emulsions or micro-emulsions of the O/W or W/O type, or also multiple emulsions such as O/W/O), body oils, foot cremes, hair setting lotions, hairsprays or alcohol or alcohol-water solutions for application to the skin.

Preferred deodorants according to the invention come in an application form selected from the group comprising sticks, crémes, gels, lotions, foams, roll-on preparations (e.g. roll-on gels, roll-on emulsions), powder sprays, aerosol or non-aerosol sprays (pump sprays).

Preference is given to sticks, roll-on preparations and sprays, since these allow the preparations containing one or more compounds of formula (I) or perfume oils according to the invention to provide the strongest and most effective sense of antimicrobial effect, hygiene and cleanliness.

Accordingly particularly preferred cosmetic preparations according to the invention are deodorants and/or antiperspirants.

The preferred deodorants and antiperspirants according to the present invention comprising one or more compounds of formula (I) preferably, depending on the way in which they work, contain one, two, three or more of the following substances:
1.) Deodorants
1-1.) Antimicrobial acting substances, which inhibit the development of the micro-organisms responsible for the smell of sweat. Examples of these are Triclosan® (5-chloro-2-(2,4-dichlorophenoxy)phenol), triclocarban, chlorhexidine, chlorhexidine hydrochloride, chlorhexidine gluconate, 2-phenoxy ethanol, farnesol, glycerine esters and ethers such as glycerine monolaurate, glycerine monocaprinate, hexoxyglycerin, octoxyglycerin (=ethylhexylglycerin, 3-(2-ethylhexyloxy-1,2-propandiol), e.g. Sensiva® SC 50 from Schülke & Mayr), aliphatic 1,2-dioles such as 1,2-decandiol (EP 1 269 983), aralipathic alcohols such as those described in WO96/19428, preferably 4-methyl-4-phenyl-2-pentanol (Vetikol; WO 03/024907) or 2-methyl-4-phenyl-2-butanol (1,1-dimethyl-3-phenylpropanol, alpha,alpha-dimethylphenethylcarbinol), l-menthylmethylether as described in WO 02/41861, 2-benzylheptan-1-ol (jasmol; 2-n-pentyl-3-phenylpropan-1-ol), 2,2-dimethyl-3-phenylpropanol (muguet alcohol; c.f. U.S. Pat. No. 4,091,090), antimicrobially-acting secondary alcohols, such as those described in WO 2005/004601, in particular 3-methyl-6-phenyl-2-hexanol, 4-(2,4-dimethylphenyl)-2-butanol, 6-(4-isopropylphenyl)-3-methyl-2-hexanol, 4-(2,4,5-trimethylphenyl)-2-butanol, 3,3-dimethyl-4-phenyl-2-butanol, 3-methyl-4-(2-methylphenyl)-2-butanol, 3-methyl 4-(2,4,5-trimethylphenyl)-2-butanol, 3,3-dimethyl-4-(2,5-dimethylphenyl)-2-butanol, 3-methyl-4-(4-methylphenyl)-2-butanol, 4-(3,4-dimethylphenyl)-3-methyl-2-butanol, 4-(3,4-dimethylphenyl)-2-butanol, 4-(2,4,6-trimethylphenyl)-2-butanol, 4-bicyclo[2.2.1]kept-2-yl-2-butanol, 3-methyl-4-(2,4,6-trimethylphenyl)-2-butanol, 4-(2,6,6-trimethylbicyclo[3.1.1]hept-3-yl)-2-butanol, 5,5-dimethyl-6-(3-methylphenyl)-hexan-2-ol, 4-bicyclo[2.2.1]hept-2-yl-3-methyl-2-butanol, 3,3-dimethyl-4-(2,4,6-trimethylphenyl)-2-butanol, 4-(4-t-butylphenyl)-3-methyl-2-butanol, 4-(4-isopropylphenyl)-3-methyl-2-butanol, 6-(3,4-dimethylphenyl)-3-methyl-2-hexanol, 4-(2,4-dimethylphenyl)-3-methyl-2-butanol, 6-(3,4-dimethylphenyl)-2-hexanol, aliphatic carboxylic acids such as 2-hexyloctanoic acid, 2-hexyldecanoic acid, 2-butyloctanoic acid or 2-butyldecanoic acid.

1-2.) Enzyme-inhibiting substances, which suppress the effect of enzymes involved in the formation of the smell of sweat. Examples of this are citric acid esters and metal-chelating substances such as EDTA (ethylene diamine tetra—acetic acid), EGTA (ethylene glycol tetra acetic acid) and DTPA (diethylene triamine pentaacetic acid—pentetic acid).

1-3.) Odor-absorbers that absorb the substances responsible for the smell of sweat. An example of this is zinc riconoleate.

1-4.) Odor-neutralizing substances, which due to their special characteristics, are able to reduce olfactory perception, for example menthyl acetate, isomenthyl acetate (as described in WO 01/43784), 2-methylpropionic acid-3-hydroxy-2,2-dimethyl-1-(1-methylethyl)-propylester and/or 2-methylpropionic acid-3-hydroxy-2,2,4-trimethylpentylester, accords and perfume oils as described in EP 2 014 273, DE 10 2008 043 586.

1-5.) Odor-masking substances, which due to their strong odor and their odor type are able to mask the smell of sweat. Examples are quoted in, for example WO 2006/124230. In anhydrous cosmetic preparations, these substances can be used in spray-dried or encapsulated form, e.g. using cyclodextrin.

2.) Antiperspirants

Antiperspirants inhibit the secretion of sweat and thus remove the bacteria responsible for body odor from the breeding ground. As antiperspirants astringent metal salts are generally used, in particular inorganic and organic metal salts of the elements aluminum, zinc, magnesium, tin and zirconium as well as mixtures of these, wherein in particular halogenides such as aluminum hydroxychloride, zirconyl oxychloride and zirconyl hydroxychloride as well as mixtures of these are used. Frequently these aluminum and zirconium salts and their mixtures are also used in complex form, with propylene glycol, polyethylene glycol or glycerine being used as complexing agents.

Here the following antiperspirants or mixtures of these are preferred:
aluminium chlorohydrate; aluminium sesquichlorohydrate, aluminium chlorohydrex PG, aluminium dichlorohydrex PG, aluminium sesquichlorohydrex PG, aluminium chlorohydrex PEG, aluminium dichlorohydrex PEG, aluminium sesquichlorohydrex PEG, aluminium chloride (preferably in the form of a 15% by weight (aqueous) solution), aluminium zirconium chlorohydrate, aluminium zirconium trichlorohydrate, aluminium zirconium tetrachlorohydrate, aluminium zirconium pentachlorohydrate, aluminium zirconium octachlorohydrate, aluminium zirconium trichlorohydrex-gly, aluminium zirconium tetrachlorohydrex-gly, aluminium zirconium pentachlorohydrex-gly, aluminium zirconium octachlorohydrex-gly, buffered aluminium sulphate, basic aluminium chloride, zirconium hydroxychloride, zirconium chloride, basic aluminium nitrate, basic aluminium chloride combined with zirconyloxychloride and -hydroxychloride, organic complexes of basic aluminium chlorides and/or zirconium chloride and/or zirconium hydroxychloride.

In turn, preference here is for aluminum or aluminum zirconium complexes with a metal/anion ratio in the range 0.9:1 to 2.1:1, wherein the anion is preferably selected from the group comprising $Cl^-$, $Br^-$, $I^-$ and/or $NO_3^{-1}$, if necessary in combination with additives such as amino acids (preferably glycine) or mono- or polyvalent alcohols. The polyvalent alcohols are preferably di-, tri- or polyols with 3-12 C-atoms, with preference here being in turn for glycerine, propylene glycol, diglycerine tripropylene glycol, sorbitol, 1,2,4-butantriol or 1,2,6-hexantriol and mixtures thereof, with particular preference for glycerine and digycerine. Advantageous monoaicohols are glycol ethers such as monoalkylether or alpha-hydroxy acids such as lactic acid.

In connection with the present invention mixtures of antiperspirants comprising (i) aluminum and/or zirconium and (ii) zinc and/or tin can be used, such as Al/Zr/Zn, Al/Zn, Al/Sn or Al/Sr/Sn, wherein mixtures comprising one or more antiperspirants from among the abovementioned preferred aluminum- and or zirconium-based antiperspirants are in turn preferred.

If necessary the deodorants and antiperspirants according to the invention, apart from the special active ingredients described above, can contain additional substances:
propellant gases, ethanol, propylene glycol, emulsifiers such as aminomethylpropanol, skin care/moisturising agents such as 2-octyldodecanol, isopropylmyristate, isopropylpalmitate, stearamide, sorbitol, glycerine and modified polyethylene- and polypropylenglycols, vitamins and their derivatives (e.g. tocopherol (vitamin E), tocopheryl acetate (vitamin E-acetate) and ascorbic acid (vitamin C)), panthenol, allantoine, plant extracts, such as Aloe Vera and proteins, lustre agents, electrolyte salts such as KCl, NaCl, gelling substances such as hydroxyalkylcelluloses, fatty alcohols, fatty acids, fatty alcohol fatty acid esters, fatty acid glyceryl esters or similar, liquid carriers and solvents such as volatile and non-volatile silicon oils, solid carriers such as talcum, silica gels, and similar; antioxidants and preservatives, UV-light protective filters, cooling agents, additional fragrancing materials, in order to modify odor types, which increase sensory acceptance and/or improve the hedonistic feeling.

Preferably (topical) cosmetic or pharmaceutical products according to the invention comprise additionally one, two, three, four or further substances which are primarily used to inhibit growth of undesired microorganisms. Further active ingredients which may be preferably used in this respect are those products of particular relevance in the field of cosmetics, namely Triclosan® (5-chloro-2-(2,4-dichlorophenoxy) phenol), climbazole, zinc pyrithione, ichthyol, Octopirox (1-hydroxy-4-methyl-6-(2,4,4-trimethylpentyl)-2(1H)-pyridone, 2-aminoethanol), chitosan, farnesol, hexoxyglycerin, octoxyglycerin (=ethylhexylglycerin, 3-(2-ethylhexyloxy-1, 2-propanediol), for example Sensiva® SC 50 from Schüike & Mayr), glycerol monolaurate, arylalkyl alcohols such as for example 2-phenylethyl alcohol, 3-phenyl-1-propanol, veticol (4-methyl-4-phenyl-2-pentanol) or muguet alcohol (2,2-dimethyl-3-phenylpropanol), polyglycerol esters, such as for example polyglyceryl 3-caprylate, aliphatic 1,2-diols such as for example 1,2-pentanediol, 1,2-hexanediol, 1,2-octanediol, and 1,2-decanediol and alkyl-branched carboxylic acids such as 2-butyloctanoic acid, 2-butyldecanoic acid, 2-hexyloctanoic acid and 2-hexyldecanoic acid or combinations of the stated substances, which are used inter alia against underarm odor, foot odor or dandruff.

Cosmetic and pharmaceutical, preferably dermatological, preparations according to the invention in many cases advantageously contain one, two, three, four or more preservatives. Preservatives which are preferably selected are those such as benzoic acid and the esters and salts thereof, 4-hydroxybenzoic acid and the esters ("parabens") and salts thereof, propionic acid and the esters and salts thereof, salicylic acid, and the esters and salts thereof, 2,4-hexadienoic acid (sorbic acid) and the esters and salts thereof, tropolone, 4-methylbenzyl alcohol (preferably 4-methylbenzyl alcohol in a mixture with 1,2-hexanediol and 1,2-octanediol as described in WO 2008/119841), formaldehyde and paraformaldehyde, 2-hydroxybiphenyl ether and the salts thereof, 2-zinc sulfidopyridine N-oxide, inorganic sulfites and bisulfites, sodium iodate, chlorobutanol, 4-ethylmercury(II) 5-amino-1,3-bis(2-hydroxybenzoic acid), the salts and esters thereof, dehydracetic acid, formic acid, 1,6-bis(4-amidino-2-bromophenoxy)-n-hexane and the salts thereof, the sodium salt of ethylmercury (II) thiosalicylic acid, phenylmercury and the salts thereof, 10-undecenoic acid and the salts thereof, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly(hexamethylene biguanide) hydrochloride, 2-phenoxyethanol, hexamethylene tetramine, 1-(3-chloroallyl)-3,5,7-triaza-1-azonia adamantine chloride, 1-(4-chlorophenoxy)1(1H-imidazol-1-yl)-3,3-dimethyl-2-butanone, 1,3-bis(hydroxymethyl)-5,5-dimethyl-2,4-imidazolidindione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H)isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$) trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidino-phenoxy)-n-hexane and the salts thereof, glutaraldehyde, 5-ethyl-1-aza-3,7-dioxabicyclo(3.3.0)octane, 3-(4-chlorophenoxy)-1,2-propanediol, Hyamine, alkyl-($C_8$-$C_{18}$)-dimethylbenzylammonium chloride, alkyl-($C_8$-$C_{18}$)-dimethylbenzylammonium bromide, alkyl-($C_8$-$C_{18}$)-dimethylbenzylammonium saccharinate, benzylhemiformal, 3-iodo-2-propynyl butylcarbamate, sodium hydroxymethylaminoacetate or sodium hydroxymethylaminoacetate.

In preferred embodiments, in particular in (topical) cosmetic or pharmaceutical products, the compounds of formula (I) of the present invention are combined with one, two or more compounds selected from the group consisting of:
(i) branched or unbranched 1,2-alkanediols having 3 to 14 carbon atoms,
(ii) benzoic acid (INCI: Benzoic Acid) and its esters and salts,
(iii) 4-hydroxybenzoic acid and its esters (INCI: Parabens) and salts,
(iv) 2,4-hexadienoic acid (INCI: Sorbic Acid) and its salts,
(v) 2-phenoxyethanol (INCI: Phenoxyethanol),
(vi) 3-iodo-2-propinyl-butylcarbamate (INCI: Iodopropynyl Butylcarbamate),
(vii) 3-(4-chlorphenoxy)-1,2-propane-1,2-diol (INCI: Chlorphenesin),
(viii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxy-methylurea (INCI: Diazolidinyl Urea) and N-(4-chlorophenyl)-N'-(3,4-dichlorophenyl)-urea (INCI: Triclocarban),
(xi) 1,3-bis-(hydroxymethyl)-5,5-dimethyl-2,4-imidazolidindione (INCI: DMDM hydantoin),
(x) 1,2-propanediol, 3-(2-ethylhexyloxy) (INCI: Octoxyglycerin),
(xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone)
(xii) 4-methylbenzyl alcohol (preferably 4-methylbenzyl alcohol in a mixture with 1,2-hexanediol and 1,2-octanediol as described in WO 2008/119841).

Odor absorbers are for example the phyllosilicates described in DE 40 09 347, of these in particular montmorilonite, kaolinite, nontronite, saponite, hectorite, bentonite, smectite, furthermore for example zinc salts of ricinoleic acid. These also include bactericidal or bacteriostatic deodorizing substances, such as for example hexachlorophene, 2,4,4'-trichloro-2'-hydroxydiphenyl ether (Irgasan), 1,6-di-(4-chlorophenyldiguanidino)hexane (chlorhexidine), 3,4,4'-trichlorocarbanilide, and the active agents described in published patent applications DE-37 40 186, DE-39 38 140, DE-42 04 321, DE-42 29 707, DE-42 29 737, DE-42 37 081, DE-43 09 372, DE-43 24 219, and contain cationically active substances, such as for example quaternary ammonium salts and odor absorbers, such as for example Grillocin® (combination of zinc ricinoleate and various additives) or triethyl citrate, optionally in combination with ion-exchange resins.

For some applications it is advantageous to use the compounds of formula (I) or a perfume oil comprising one or more compounds of formula (I) according to the invention adsorbed by a carrier that ensures both the distribution in the product and a controlled release when applied. Such carriers may be porous inorganic materials such as light grade sulphate, silica gels, zeoliths, gypsum, clays, granulated clay, gas concrete and so on, or organic materials such as woods, cellulose-based materials, sugar or plastics such as PVC, polyvinyl acetate or polyurethane.

For other applications it is advantageous to use the compounds of formula (I) or a perfume oil comprising one or more compounds of formula (I) according to the invention in micro-encapsulated and spray-dried form or as an inclusion complex or extrusion product.

The characteristics of such modified (perfumed) mixtures are in many cases optimized by coating with suitable materials to achieve a more targeted scent release, for which preferably waxy plastics such as polyvinyl alcohols are used.

The microencapsulation of the compounds of formula (I) or a perfume oil comprising one or more compounds of formula (I) according to the invention can, for example, take place by means of the so-called coacervation method with the help of capsule materials such as polyurethane-like materials or soft gelatine The spray-dried perfume oils according to the invention can, for example, be manufactured by spray drying of an emulsion or dispersion containing the perfume oil, wherein for the carrier modified starches, proteins, dextrin and vegetable gums can be used. Inclusion complexes can, for example, be manufactured by introducing dispersions of the perfume oil and cyclodextrins or urea derivatives into a suitable solvent, such as water. Extrusion products can be created by melting the perfume oils with a suitable waxy substance followed by extrusion and subsequent hardening, if necessary in a suitable solvent, such as isopropanol.

In the methods and uses according to the invention it is preferable for application to be on the human skin and/or hair. In many cases a method according to the invention is preferred in which the application takes place in the presence of perceptible body odor. Likewise preferred with the method according to the invention is that the application takes place in the area of a source or a potential source of body odor. A source or potential source can in particular be considered to be the armpits.

In addition, it was found that the compounds of formula (I) of the present invention show a bactericidal action against oral care relevant microorganisms, in particular against *Porphyromonas gingivalis* and *Streptococcus mutans*, which play a role in plaque and plaque formation and in the cariogenic process (i.e. the development of caries) and tooth decay, i.e. the compounds of formula (I) were also found active against parodontitis and/or gingivitis, and to be able to inhibit and/or reduce the formation of parodontitis and/or gingivitis.

Periodontitis (parodontitis) is an inflammation of the periodontium, in other words the tissues that surround and support the teeth. The periodontium comprises various tissues: the gum epithelium (gingiva), the connective tissue of the gingiva, the periodontal ligament (desmodontium), the cementum and the surrounding alveolar bone. The main clinical features of periodontitis include inflammation of the gums, attachment loss, formation of periodontal pockets and degradation of the alveolar bone.

The main cause of periodontitis is plaque. This consists of certain components of saliva, food residues and above all bacteria and their decomposition products. The continuous release of bacterial toxins presumably triggers the distribution of proinflammatory mediators, such as IL-1 beta, TNF-alpha and PGE2 for example, in the patient's affected tissues. The reaction of the body is the inflammation of the gingiva and the periodontium with damage to the alveolar bone. In the final stage of periodontitis the affected person is at risk of a massive loss of teeth.

In particular, the compounds of formula (I) and oral hygiene products according to the invention are capable of inhibiting and/or preventing the growth of microorganisms in the oral cavity and/or of killing these, in particular those chosen from the group consisting of: *Porphyromonas* and *Streptococcus* species, in particular *Porphyromonas gingivalis, Streptococcus sobrinus* and *Streptococcus mutans* which play an important role in the formation of parodontitis and/or gingivitis.

Thus, a further aspect of the present invention relates to formulations according to the invention in the form of oral care products (oral hygiene products). An oral care product (also called oral hygiene product) in the context of the invention is understood as meaning one of the formulations familiar to the person skilled in the art for cleansing and care of the oral cavity and the pharyngeal cavity and for refreshing the breath. This expressly includes care of the teeth and gums. Presentation forms of the usual oral hygiene formulations are creams, gels, pastes, foams, emulsions, suspensions, aerosols and sprays, and also capsules, granules, pastilles, tablets, candies or chewing gums, without this list being intended to be understood as limiting for the purpose of this invention.

Preferred oral care products are in particular dental care products such as toothpastes, dental creams, dental gels, dental powders, tooth-cleaning liquids, tooth-cleaning foams, mouthwashes, dental cream and mouthwash as a 2-in-1 product, sugar-free candies for sucking, oral sprays, dental floss or dental care chewing gums. The activity of the formulations according to the invention also manifests itself remarkably well in the field of oral hygiene.

Dental care compositions (as a preferred example of an oral care product according to the invention) in general comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavor correctants for unpleasant taste impressions, flavor correctants, flavor-modulating substances (e.g. inositol phosphate, nucleotides, such as guanosine monophosphate, adenosine monophosphate or other substances, such as sodium glutamate or 2-phenoxypropionic acid), fresh breath imparting substances, bad breath reducing/combating substances (preferably selected from those described in WO 2006/032668 or EP 1 886 662 A1), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan (2,4,4'-trichlor-2'-hydroxydiphenyl ether), cetylpyridinium chloride, aluminium lactate, potassium citrate, potassium nitrate, potassium chloride, strontium chloride, hydrogen peroxide, flavors, sodium bicarbonate and/or odor correctants.

Preferred sugar-free bases for oral care products, generally include bulk sweeteners such as isomalt, maltitol, sorbitol and xylitol.

Chewing gums (as a further example of formulations according to the invention far oral care) which comprise one or more compounds of formula (I) according to the invention in general comprise a chewing gum base, i.e. a chewing composition which becomes plastic on chewing, various types of sugar substitutes, sweeteners, other sweet-tasting substances, sugar alcohols (in particular sorbitol, xylitol, mannitol), optionally cooling active compounds, flavor correctants for unpleasant flavor impressions, flavor modulators, moisture-retaining agents, thickeners, emulsifiers, aromas and stabilizers or smell correctants.

Formulations according to the invention in the form of chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. No. 4,518, 615, U.S. Pat. No. 5,093,136, U.S. Pat. No. 5,266,336 U.S. Pat. No. 5,601,858 or U.S. Pat. No. 6,986,709. In addition, chewing gum bases comprise further constituents, such as, for example, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations according to the invention (in particular those which are in the form of an oral care product) preferably additionally comprise one or more aroma and/or flavoring substances, such as essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, ginger oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the formulations according to the invention comprise at least one aroma substance, preferably 2, 3, 4, 5, 6, 7, 8, 9, 10 or more aroma substances, chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably ID-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascene, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In the context of the invention, menthol preferably is d-menthol, l-menthol or any mixture thereof, l-menthol, d-menthol and racemic menthol being preferred and l-menthol being particularly preferred.

Peppermint oils are understood as meaning specifically the essential (i.e. obtained by means of steam distillation) oils of certain *Mentha* species, in particular from *Mentha arvensis* (field mint, also called cornmint in US language) and from *Mentha piperita* (called peppermint in US language), which include *Mentha piperita* oils with names of regional origin from specific cultivation areas, such as Willamette, Yakima and Madras.

Particularly preferred oral care products according to the invention comprise (a) one or more compounds of formula (I) according to the invention and (b) one, two, three, four all of the compounds chosen from the group consisting of (i) menthol, (ii) (−)-carvone, (iii) menthone, (iv) isomenthone and (v) menthyl acetate.

Preferred oral care products according to the invention comprise (a) one or more compounds of formula (I) according to the invention and (b) one or more physiological cooling agents, preferably selected from the group consisting of: menthone glycerol acetal (trade name: Frescolat®MGA), menthyl lactate (preferably 1-menthyl lactate, in particular 1-menthyl l-lactate, trade name: Frescolat®ML), substituted menthyl-3-carboxylic acid amides (e.g. menthyl-3-carboxylic acid N-ethylamide), 2-isopropyl-N-2,3-trimethylbutanamide, 3-menthoxypropane-1,2-diol, 2-hydroxyethyl menthyl carbonate, 2-hydroxypropyl menthyl carbonate, isopulegol and monomenthyl succinate. The total amount of cooling agents can vary depending on the sensory effects to be achieved. Preferably, an oral care composition according to the present invention comprises a total amount of cooling agents in the range of 0.05 to 5.0 wt. %, more preferably in the range of 0.1 to 3.0 wt. %, in each case based on the total weight of the oral care composition.

In another preferred method according to the invention application is by spraying.

In the following further explanations of the invention, or individual aspects of it, are provided by means of the claims and examples.

EXAMPLES

Unless otherwise stated all figures refer to the weight. Abbreviations used: DPG: dipropylene glycol, IPM=isopropyl myristate; PPG: polypropylene glycol.

In some cases trade names for perfumery materials are used, reference is made to the following suppliers:

[1] Tradename Symrise GmbH, Germany;

[2] Tradename Givaudan AG, Switzerland;

[3] Tradename IFF (International Flavors & Fragrances Inc.), USA;

[4] Tradename BASF AG, Germany;

[5] Tradename Danisco Seillans S.A., France;

[6] Tradename Kao Corp., Japan;

[7] Tradename Miltitz Aromatics, Germany;

[9] Tradename Firmenich S.A., Switzerland.

Synthesis Example 1

5-Cyclohexyl-2-n-propyl-pentanol

Synthesis Example 1.1

Synthesis of 2-n-propyl-5-phenylpenta-2,4-dienal

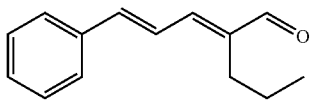

A mixture of cinnamaldehyde (400 g) and valeraldehyde (300 g) was added to a solution of 52 g of NaOH in 1950 g methanol over a period of 2 hours. After the addition is completed, stirring was continued for another 2 hours. The reaction mixture was washed with water, the solvent removed and the resulting product distilled. 412 g 2-n-Propyl-5-phenyl-penta-2,4-dienal were obtained as a yellowish oil (content 90%; 60% theoretical yield).

Spectroscopic data for 2-n-propyl-5-phenylpenta-2,4-dienal:

$^{13}$C-NMR (CDCl$_3$; 100 MHz) δ(ppm)=14.07 (CH$_3$), 22.51 (CH$_2$), 26.30 (CH$_2$), 123.42 (CH), 127.43 (CH), 128.92 (2×CH), 129.38 (2×CH), 136.10 (C), 141.21 (CH), 142.35 (C), 149.01 (CH), 194.67 (CO).

MS: m/z (%)=200 (M$^+$, 78), 185 (8), 171 (34), 157 (36), 143 (42), 128 (100), 115 (59), 104 (32), 91 (50), 77 (19).

Synthesis Example 1.2

Hydrogenation of the Reaction Product Obtained in Example 1.1

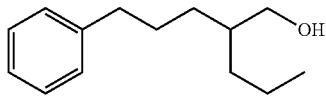

395 g of 5-Phenyl-2-n-propyl-penta-2,4-dienal from Synthesis Example 1.1 were combined with 14 g of Raney-Ni and hydrogenated at a hydrogen pressure of 20 bar and at a temperature of 120° C. After 20 hours the reaction was finished. The catalyst was removed and the product distilled. 365 g (content 96%) of 5-phenyl-2-n-propyl-pentanol are obtained. Yield: 93.6% of theoretical.

Synthesis Example 1.3

Hydrogenation of the Reaction Product Obtained in Synthesis Example 1.2

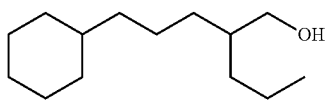

365 g of 5-Phenyl-2-n-propyl-pentanol of Synthesis Example 1.2 were combined with 10 g Ru on activated carbon (Ru content: 5 wt. %) and hydrogenated at a hydrogen pressure of 20 bar and at a temperature of 120° C. After 5-7 hours the reaction was finished. The catalyst was removed and the product distilled. 345 g (content: 98.2%) of 5-cyclohexyl-2-n-propyl-pentanol are obtained. Yield: 90.8% of theoretical.

Spectroscopic data for 5-cyclohexyl-2-n-propyl-pentanol:

$^{13}$C-NMR (CDCl$_3$; 100 MHz) δ(ppm)=65.65 (t), 40.36 (d), 37.98 (t), 37.72 (t), 33.50 (t), 33.31 (t), 31.30 (t), 26.79 (t), 26.46 (t), 24.14 (t), 20.06 (t), 14.51 (q)

MS: m/z (%)=M$^+$ ion 212(0.01), 194(4), 151(13), 109(19), 96(85), 83(66), 69(53), 55(100), 41(55).

Odor description: overall very weak, flowery, blossom, slightly fatty.

Synthesis Example 2

Hydrogenation of 2-methyl-5-phenyl-pentanol

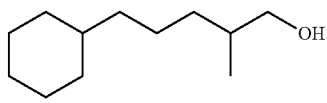

3415 g of 2-Methyl-5-phenyl-pentanol (Rosaphen™, supplier: Symrise) combined with 33 g Ru on activated carbon (Ru content: 5 wt. %) were hydrogenated at a hydrogen pressure of 20 bar and at a temperature of 100° C. After 14-17 hours the reaction was finished. The catalyst was removed and the product distilled. 3437 g (content: 99.9%) of 5-cyclohexyl-2-methyl-pentanol were obtained. Yield: 97% of theoretical.

$^{13}$C-NMR (CDCl$_3$; 100 MHz) δ(ppm)=68.19 (t), 37.86 (t), 37.71 (d), 35.79 (d), 33.55 (t,t), 33.44 (t), 26.79 (t), 26.49 (t,t), 24.25 (t), 16.63 (q)

MS: m/z (%)=166(23), 109(20), 96(90), 82(72), 67(43), 55(100), 41(48).

Odor description: overall weak, flowery, blossom, rose, lily of the valley, faintly green In direct comparison with 2-methyl-5-phenyl-pentanol (odor description: rose, geraniol) 5-cyclohexyl-2-methyl-pentanol showed overall weaker odor intensity.

Synthesis Example 3

Hydrogenation of 3-methyl-5-phenyl-pentanol

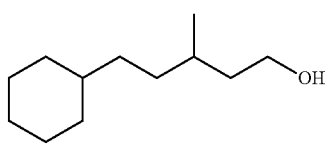

1200 g of 3-Methyl-5-phenyl-pentanol (Phenoxanol™, supplier: IFF) combined with 10.5 g Ru on aluminium oxide (Ru content 5 wt. %) were hydrogenated at a hydrogen pressure of 25 bar and at a temperature of 110° C. After 15 hours the reaction was finished. The catalyst was removed and the product distilled. 1204 g (content 99.7%) of 5-cyclohexyl-3-methyl-pentanol were obtained.

Synthesis Example 4

Hydrogenation of 5-(p-isopropylphenyl)-2-methyl-1-pentanol

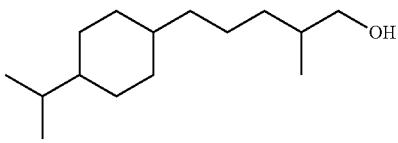 [SMILES: CC(CO)CCCC1CCC(C(C)C)CC1]

100 g of 5-(4-Isopropylphenyl)-2-methyl-1-pentanol (obtained as described in EP 0 908 439) combined with 1.5 g Ru on aluminium oxide (Ru content 5 wt. %) were hydrogenated at a hydrogen pressure of 25 bar and at a temperature of 110° C. After 15 hours the reaction was finished. The catalyst was removed and the product distilled. 100 g (content 99.7%) of 5-(4-isopropylcyclohexyl)-2-methyl-1-pentanol were obtained.

Synthesis Example 4.1

Analogously to Synthesis Example 4 the compound 5-(p-tert.-butylcyclohexyl)-2-methyl-1-pentanol was obtained starting from 5-(p-tert.-butylphenyl)-2-methyl-1-pentanol.

Synthesis Example 5

Hydrogenation of 2,4-dimethyl-5-phenyl-pentanol

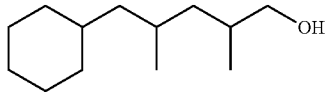

100 g of 2,4-Dimethyl-5-phenyl-pentanol (obtained as described in EP 0 908 439) combined with 2 g Ru on aluminium oxide (Ru content: 5 wt. %) were hydrogenated in 80 ml cyclohexane at a hydrogen pressure of 22 bar and at a temperature of 105° C. After 18 hours the reaction was finished. The catalyst was removed and the product distilled. 100 g (content: 99.5%) of 5-cyclohexyl-2,4-dimethyl-pentanol were obtained.

Odor description: overall very weak, flowery, blossom, faintly nutty

Synthesis Example 6

Hydrogenation of 2,4-dimethyl-6-(p-isopropylcyclohexyl)-1-pentanol

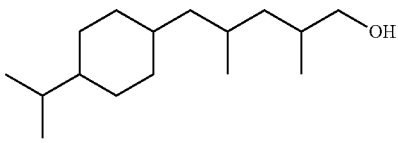 [SMILES: CC(CO)CC(C)CC1CCC(C(C)C)CC1]

100 g of 2,4-Dimethyl-5-(p-isopropylcyclohexyl)-1-pentanol (obtained as described in EP 0 908 439) combined with 1.25 g Ru on activated carbon (Ru content: 5 wt. %) were hydrogenated at a hydrogen pressure of 45 bar and at a temperature of 95° C. After 20 hours the reaction was finished. The catalyst was removed and the product distilled. 100 g (content: 99.6%) of 2,4-dimethyl-5-(4-isopropylcyclohexyl)-1-pentanol were obtained.

Synthesis Example 7

Hydrogenation of 2-methyl-5-phenyl-pentanol

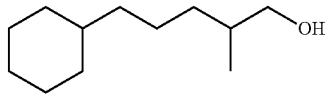

1200 g of 2-Methyl-5-phenyl-pentanol (Rosaphen™, supplier: Symrise) combined with 22 g Pd on activated carbon (Pd content: 5 wt. %) were hydrogenated at a hydrogen pressure of 50 bar and at a temperature of 120° C. After 30 hours the reaction was finished. The catalyst was removed and the product distilled. 1170 g (content: 99.6%) of 5-cyclohexyl-2-methyl-pentanol were obtained.

Assay Example 1

Determination of Minimum Inhibitory Concentration (MIC) Values

Assay Example 1.1

Method Description for MIC Determination

The observation that the compounds of formula (I) are very particularly suitable for combating microorganisms which are responsible for body odor is based on a series of investigations relating to the particularly relevant microorganisms *Staphylococcus epidermidis Corynebacterium xerosis*, and *Brevibacterium epidermidis*.

The antimicrobial action of the compounds of formula (I) is here detected with the assistance of a turbidimetric measurement method. Turbidity measurement is used to establish growth curves for the particular microorganism in the presence and absence of an antimicrobial active ingredient. A possible inhibitory action of the test substance used is identified from the profile of the growth curves. Solutions with saline or DMSO for 100% growth are prepared as a negative control.

The active substances to be investigated are first diluted in DMSO in reaction vessels. Dilution is carried out in accordance with the concentration range to be tested and corresponds in each case to 100 times the concentration of the subsequent final concentration in the test Testing is usually begun with a final concentration of 2000 ppm (corresponding to 0.2 wt.-%) in the test. Growth curves at final concentrations of 1000 ppm, 500 ppm, 250 ppm, 125 ppm, 64 ppm, 32 ppm, 16 ppm and 8 ppm are subsequently determined.

The bacterial cultures are then incubated in the presence of the various final concentrations of antimicrobial active ingredient for 16 h (incubation temperature: 37° C.). The absorption values (wavelength 620 nm; measurement interval: 20 minutes) obtained over the 16 hour period of turbidimetric measurement are recorded and exported into the spreadsheet program MS Excel. Means from in each case three parallel batches are calculated and used as the basis for establishing growth curves. The curves of the individual test sample concentrations are compared with those for the negative controls and the MIC value (minimum inhibitory concentration) is determined. The MIC value is the concentration at which no further growth is observable by turbidimetry.

Assay Example 1.2

MIC determination for
5-Cyclohexyl-2-methyl-pentanol

MIC values of 5-cyclohexyl-2-methyl-pentanol were determined in accordance with the general test conditions described in Assay Example 1.1. Complete inhibition of growth for *Staphylococcus epidermidis* (ATCC 12228) was determined at a usage concentration of just 64 ppm, so demonstrating this compound's good antimicrobial activity. It likewise proved possible to establish inhibition of the growth of further bacteria such as *Corynebacterium xerosis* (DSM 20743) and *Brevibacterium epidermidis* (ATCC 35514) causing body odor by 5-cyclohexyl-2-methyl-pentanol in a concentration of below 0.2 wt. % using the test method described in Assay Example 1.1.

The antimicrobial activity of 5-cyclohexyl-2-methyl-pentanol against *Streptococcus mutans* (ATCC25175) and *Porphyromonas gingivalis* (ATCC33277) (which cause parodontitis and gingivitis) was also measured. The MIC value of 5-cyclohexyl-2-methyl-pentanol against each of these strains was determined to be 32 ppm.

Assay Example 1.3

MIC determination of
5-Cyclohexyl-2-n-propyl-pentanol

MIC values of 5-cyclohexyl-2-n-propyl-pentanol were determined in accordance with the general test conditions described in Assay Example 1.1. Complete inhibition of growth for *Staphylococcus epidermidis* (ATCC 12228) was determined at a usage concentration of just 16 ppm, so demonstrating this compound's good antimicrobial activity. It likewise proved possible to establish inhibition of the growth of further bacteria such as *Corynebacterium xerosis* (DSM 20743) and *Brevibacterium epidermidis* (ATCC 35514) causing body odor by 5-cyclohexyl-2-n-propyl-pentanol in a concentration of below 0.2 wt. % using the test method described in Assay Example 1.1.

It furtheron proved possible to confirm the antimicrobial activity of 5-cyclohexyl-2-methyl-pentanol and 5-cyclohexyl-2-n-propyl-pentanol towards microorganisms which cause body odor such as *Corynebacterium xerosis* (DSM 20743), *Staphylococcus epidermidis* (ATCC 12228) and *Brevibacterium epidermidis* (ATCC 35514) with the assistance of the quantitative suspension test, a further in vitro method for determination of antimicrobial activity.

The antimicrobial activity of 5-cyclohexyl-2-n-propyl-pentanol against *Streptococcus mutans* (ATCC25175) and *Porphyromonas gingivalis* (ATCC33277) (which cause parodontitis and gingivitis) was also measured. The MIC value of 5-cyclohexyl-2-methyl-pentanol against each of these strains was determined to be 8 ppm.

Assay Example 2

Determination of Influence on Biofilm Formation

Assay Example 2.1

Method Description for Determination of Influence on Biofilm Formation

The recognition that the compounds of formula (I) are also very particularly suitable for either inhibition of initial biofilm formation and stagnation or even detachment of pre-existing biofilms is based on a series of investigations relating to the particularly relevant microorganism *Corynebacterium xerosis*.

The antimicrobial action of the compounds of formula (I) on biofilms is hereby detected with the assistance of a staining method. Crystal violet staining is used to quantify amount of biofilm in the presence and absence of an antimicrobial active ingredient. A possible inhibitory action of the test substance used is identified from the staining profile.

*Corynebacterium xerosis* can adhere to artificial laboratory surfaces and contribute to biofilm formation much the same way as it can do on skin in vivo. Therefore we furtheron established a test system to evaluate the influence of antimicrobial active compounds of formula (I) on *Corynebacterium xerosis* forming a biofilm or already residing in a biofilm.

Growth Assay

Under laboratory conditions (96-well microtiterplates) the gram-positive bacterium *Corynebacterium xerosis* takes 24 hours to reach stationary growth phase. Biofilm formation can be analyzed by crystal violet staining with subsequent spectroscopic quantitation at 580 nm ($CV_{580}$).

*Corynebacterium xerosis* (DSM 20743, ATCC 373) was cultivated in M53 standard medium containing peptone, yeast-extract and glucose. Static incubation of 0.2 ml cultures in flat-bottom 96-well microtiterplates at 37° C. for 18-24 h or until the untreated control reached stationary phase. Experiments were conducted with fresh over-night cultures diluted to $OD_{580}$ 0.1 with fresh medium prior to use.

Test compounds were dissolved in DMSO and added at a final concentration of 12.5 µg/ml. DMSO was present in all assays and did not significantly effect cell growth at the given concentration (2.5%).

In order to identify potential anti-biofilm bioactives the following two growth assay formats (a: classic assay and b: mid-log assay) have been established. Test and substances were added either directly after inoculation of 96-well microtiterplate (a: classic assay) or after cells had reached an optical density corresponding to half-maximal $OD_{580}$ (b: mid-log assay).

a) Classic assay: allows identification of anti-microbial bioactives, which target prevention of biofilm formation.

Anti-microbial testing of *Corynebacterium xerosis* has been conducted in growth assay format with simultaneous initial addition of test compounds and inoculum. This allowed monitoring any effects on biofilm formation. Anti-microbial effects of test compounds on biofilm formation was determined by $CV_{580}$ crystal violet staining 18-24 hours after inoculation and several washing steps that are needed to separate planctonic grown microorganisms.

b) Mid-log assay: leads to identification of bioactives, which target cells residing in a pre-existing biofilm.

In contrast to the classic assay format, cells were first grown to half-maximum biofilm formation before test compounds were added to a final concentration of 12.5 µg/mL. This approach allows for efficacy testing of screening compounds on cells residing in a pre-formed biofilm and monitoring potential biofilm-disrupting activities. Cultivation was continued for additional 12-18 hours. Optical density $OD_{580}$ was then measured followed by crystal violet staining and spectroscopic quantitation of the biofilm at 580 nm ($CV_{580}$). Mid-log time point was determined by cultivating untreated *C. xerosis* cells on separate control plates. $CV_{580}$ crystal violet staining data of untreated control cells at mid-log were recorded. Additional control cells were further cultivated until cells entered stationary phase and showed no further increase in biofilm formation. $CV_{580}$ of untreated control samples was also recorded. $CV_{580}$ measurements of test compounds were plotted in relation to the mid-log values of control cells, which was arbitrarily set 100%. Thus, untreated control cells will reach a value of 200%, corresponding to twice the exactly determined mid-log time point (half-maximal values for $CV_{580}$; which was set 100%).

The experimental results (%-values) achieved in the presence of an antimicrobial active agent on biofilm properties thus can be interpreted in the following way in the mid-log assay:

| | |
|---|---|
| 200% | test compound has no effect on biofilm |
| 200%-100% | test compound leads to retardation of biofilm formation |
| 100% | test compound leads to stagnation of biofilm formation |
| <100% | test compound leads to detachment and lysis of biofilm |

Exponentially growing cells (mid-log) are hereby in a defined active state with respect to proliferation and metabolic activity and cell numbers are significantly higher compared to the classic assay format. The mid-log assay format thus resembles the in vivo situation more closely and allows identification of bioactives that target biofilm-protected persistent cells.

Assay Example 2.2

Determination of Influence of 5-Cyclohexyl-2-methyl-pentanol on Biofilm Formation a) Classic assay (allows identification of anti-microbial bioactives, which target prevention of biofilm formation).

In the classic assay, $CV_{58}$, measurement revealed that 12.5 µg/ml 5-cyclohexyl-2-methyl-pentanol abolished biofilm formation almost completely (92%). 8% biofilm was observed in the presence of 5-cyclohexyl-2-methyl-pentanol compared to the untreated control, with a $CV_{580}$ that was set arbitrarily to 100%.

b) Mid-log assay (leads to identification of bioactives, which target cells residing in a pre-existing biofilm)

The mid-log assay showed that biofilm treatment with 5-cyclohexyl-2-methyl-pentanol leads to cell lysis and biofilm detachment revealing robust biofilm activity. In the presence of 12.5 µg 5-Cyclohexyl-2-methyl-pentanol 53% of biofilm was observed compared to the untreated control, which was set arbitrarily to 200%, meaning that even detachment and lysis (per definition at <100%) of pre-existing biofilm took place.

Assay Example 2.3

Determination of Influence of 5-Cyclohexyl-2-n-propyl-pentanol on Biofilm Formation a) Classic assay (allows identification of anti-microbial bioactives, which target prevention of biofilm formation).

In the classic assay, $CV_{580}$ measurement revealed that 12.5 µg/ml 5-cyclohexyl-2-n-propyl-pentanol abolished biofilm formation to 65%. 35% biofilm was observed in the presence of 5-cyclohexyl-2-methyl-pentanol compared to the untreated control, with a $CV_{580}$ that was set arbitrarily to 100%.

b) Mid-log assay (leads to identification of bioactives, which target cells residing in a pre-existing biofilm)

The mid-log assay showed that biofilm treatment with 12.5 µg/ml 5-cyclohexyl-2-n-propyl-pentanol leads to stagnation of further biofilm formation revealing robust biofilm growth inhibitory activity. In the presence of 12.5 µg 5-cyclohexyl-2-n-propyl-pentanol 100% of biofilm was observed compared to the untreated control, which was set arbitrarily to 200%, meaning that any further growth of pre-existing biofilm (per definition at 100%) was completely inhibited.

In Vivo Example 1

In Vivo Human Sniffing Test for Determination of Deodorant Efficacy

In Vivo Example 1.1

Method Description for Determination of Deodorant Efficacy

The relevance of in vitro results on the antimicrobial activity of the compounds of formula (I) described in Assay Examples 1 and 2 was furtheron investigated in human clinical sniffing tests. Thereby the efficacy of a deodorant spray comprising 5-cyclohexyl-2-methyl-pentanol on the reduction of body odour was investigated with the following assay protocol:

Human in vivo sniffing test protocol for comparison of a deodorant spray comprising 0.3 wt.-% 5-cyclohexyl-2-methyl-pentanol versus untreated axillae.

The body odor reducing effect of deodorant sprays comprising antimicrobial compounds according to the invention was determined by olfactory assessment of the armpits of a group of 20 healthy male and female volunteers with distinct perspiration odor by applying the following test protocol:

During a 10 days pre-conditioning period and during the whole treatment period the volunteers were only allowed to use unscented soap without anti-bacterial ingredient and no anti-perspirant/deodorant or cosmetics. The subjects were further told to wear clothing not treated with perfumed detergent or softener. For quantification of the sensory data achieved by the volunteers, odor scores on a 0-5 scale (0=none; 1=very low; 2=low; 3=moderate; 4=high; 5=very high) were determined at different time intervals. For getting the baseline levels (t0__6h and t0__24h, see table Vivo1), armpits were sniffed on day 11 by the volunteers. After the preconditioning phase a water/ethanol (60 wt.-%:40 wt.-%) deodorant spray formulation comprising 0.3 wt-% of antimicrobial active ingredient was used (application amount: approx. 250 mg/application). Sweat odor reduction at untreated axillae and at axillae treated with deodorant spray was assessed by the volunteers. The 20 volunteers randomly applied the deodorant spray comprising antimicrobial active ingredient through the whole test period either on the right or on the left armpits, whereas the other armpit remained untreated. The first sniffing assessments were made 6 hours (t1__6h) and 24 hours (t1__24h) after a single deodorant application. After the 24 hour assessment, the subjects applied the deodorant twice a day in the morning and in the evening for 4 days. Also during that time the subjects were only allowed to use unscented soap without antibacterials and no anti-perspirant/deodorant or cosmetics. After 4 days final sniffing assessments were made again by the volunteers 6 hours (t11__6h) and 24 hours (t11__24h) after the last application. Finally, mean values of odour score ratings of volunteers at different times and odour score reduction versus initial values both after 6 hours and after 24 hours after a single application and after 11 applications were determined.

In Vivo Example 1.2

Determination of Deodorant Efficacy of 5-Cyclohexyl-2-methyl-pentanol

The clinical human in vivo sniffing study performed according to the protocol described in 5.1. showed that the deodorant spray formulation comprising 0.3 wt.-% 5-cyclohexyl-2-methyl-pentanol exhibits a highly efficient sweat odor reduction.

A highly significant odor reduction could be achieved 6 hours and 24 h after the first application (t1__6h=−1.14 and t1__24h=−0.81). In contrast untreated axillae even showed an increase in odor scores (t1__6h=+0.16 and t1__24h=+0.24)

After an application phase of 4 days, the deodorant spray comprising 0.3% 5-cyclohexyl-2-methyl-pentanol provides also a significant odor reduction 6 h after last application but also for a minimum of 24 hours after last application (t11__6h=−1.24 and t11__24h=0.91). In contrast untreated axillae again even showed an increase in odor scores (t11__6h=+0.19 and t11__24h=+0.28)

In conclusion a significant reduction in odour scores compared to the non treated axillae was observed and 24 h deodorant efficacy could be achieved after single but also after repeated treatment. The mean odour score values of the 20 volunteers treated with deodorant spray comprising 5-cyclohexyl-2-methyl-pentanol versus untreated axillae are expressed in table Vivo1.

TABLE VIVO1

Human in vivo sniffing test, volunteer ratings (mean value odor scores; 20 volunteers; visual analog scale with odor scores from 0 to 5 with 0 = no odor up to 5 = very strong odor)

|  | t0__6 h | t0__24 h | t1__6 h | T1__24 h | t11__6 h | t11__24 h |
|---|---|---|---|---|---|---|
| Untreated Axillae | | | | | | |
| mean value odor score (20 volunteers) | 3.19 | 3.48 | 3.35 | 3.71 | 3.38 | 3.76 |
| mean value odor score difference to initial at t0__6 h and t0__24 h (20 volunteers) | | | +0.16 | +0.23 | +0.19 | +0.28 |
| Axillae treated with deodorant comprising 0.3 wt.-% 5-cyclohexyl-2-methyl-pentanol | | | | | | |
| mean value odor score (20 volunteers) | 3.19 | 3.48 | 2.05 | 2.67 | 1.95 | 2.57 |
| mean value odor score difference to initial at t0__6 h and t0__24 h (20 volunteers) | | | −1.14 | −0.81 | −1.24 | −0.91 |

Example P1

Perfume Oil for Use in Deodorants and Antiperspirants (not According to the Invention)

| Components | Parts by weight |
|---|---|
| 10-Undecenal, 10% in DPG | 2.00 |
| Vertocitral (2,4-dimethyl-3-cyclohexencarboxaldehyde) | 0.50 |
| Cis-3-hexenyl acetate, 10% in DPG | 7.50 |
| Allylamylglycolate | 2.00 |
| Melonal (2,6-dimethyl-5-hepten-1-al) | 0.50 |
| Bergamot oil | 70.00 |
| Dihydromyrcenol | 80.00 |
| Cyclogalbanate (allylcyclohexyloxy acetate) | 20.00 |
| Terpinyl acetate | 40.00 |
| *Litsea cubeba* oil | 2.00 |
| Lemon oil | 50.00 |
| Orange oil | 20.00 |
| Grapefruit oil | 10.00 |
| Lavandin oil abrialis | 10.00 |
| Isobornyl acetate | 3.00 |
| Lilial (2-methyl-3-(4-tert-butyl-phenyl)propanal) | 10.00 |
| Calone 1951 (7-methyl-2H-1,5-benzodioxepin-3(4H)-one) | 2.50 |
| Florhydral (3-(3-isopropylphenyl)butanal) | 1.50 |
| Florol (2-isobutyl-4-methyltetrahydro-2H-pyran-4-ol) | 12.00 |
| Tetrahydrolinalool | 75.00 |
| *Geranium* oil | 5.00 |
| Isodamascon(1-(2,4,4-trimethyl-2-cyclohexen-1-yl)-2-buten-1-one), 10% in DPG | 2.00 |
| Resedafol, 10% in DPG [2-(1-propoxy-etboxy)ethyl]benzol | 1.00 |
| Methyl dihydrojasmonate (Hedione HC) | 158.00 |
| L-menthylmethylether | 50.00 |
| Jessemal (3-butyl-5-methyl tetrahydro-pyran-4-yl-acetate) | 4.00 |
| Benzyl salicylate | 10.00 |
| Anethol | 3.00 |
| Methylcedrylketone | 50.00 |
| Iso E Super[3] (octahydro-2,3,8,8-tetramethyl-2-acetonaphthone and 2-acetyl-1,2,3,4,6,7,8-octahydro-2,3,8,8-tetramethylnaphthaline) | 25.00 |
| Ambrocenide ((4aR,5R,7aS,9R)-octahydro-2,2,5,8,8,9a-hexamethyl-4H-4a,9-methanoazuleno(5,6-d)-1,3-dioxol), 1% in DPG | 3.00 |
| Timberol (1-(2,2,6-trimethylcyclohexyl)hexan-3-ol) | 2.00 |
| Patchouli oil | 3.50 |
| Evernyl (methyl-2,4-dihydroxy-3,6-dimethylbenzoate) | 1.50 |
| Labdanum absolute, 20% in DPG | 2.00 |
| Amber Core (1-[[2-(1,1-dimethylethyl)cyclohexyl]oxy]-2-butanol) | 10.00 |
| Ambraketal (dodecahydro-3,8,8,11a-tetramethyl-5H-3,5a-epoxynaphth[2,1-c]oxepin) | 1.50 |
| Hydroxyambran (2-cyctododecylpropanol), 50% in DPG | 5.00 |

| Components | Parts by weight |
|---|---|
| Macrolide (15-cyclopentadecanolide) | 35.00 |
| Globalide (15-pentadec-(11/12)-enolide) | 20.00 |
| Globanone ((E/Z)-8-cyclohexadecenone) | 20.00 |
| Isopropylmyristate (IPM) | 170.00 |
| Total | 1,000.00 |

Example P2

Perfume Oil Having "Rose" Odor (not According to the Invention)

| Components | Parts by weight |
|---|---|
| Acetophenone, 10% in DPG | 10.00 |
| n-Undecanal | 5.00 |
| Aldehyde C14 so-called (peach aldehyde) | 15.00 |
| Allylamylglycolate, 10% in DPG | 20.00 |
| Amylsalicylate | 25.00 |
| Benzyl acetate | 60.00 |
| Citronellol | 80.00 |
| d-Limonene | 50.00 |
| Trans-9 decenol | 15.00 |
| Dihydromyrcenol | 50.00 |
| Dimethylbenzyl carbinyl acetate | 30.00 |
| Diphenyl oxide | 5.00 |
| *Eucalyptus* oil | 10.00 |
| Geraniol | 40.00 |
| Nerol | 20.00 |
| *Geranium* oil | 15.00 |
| Hexenol cis-3, 10% in DPG | 5.00 |
| Hexenyl salicylate cis-3 | 20.00 |
| Indol, 10% in DPG | 10.00 |
| Alpha-Ionone | 15.00 |
| Beta-Ionone | 5.00 |
| Lilial (2-methyl-3-(4-tert-butyl-phenyl)propanal) | 60.00 |
| Linalool | 40.00 |
| Methylphenyl acetate | 10.00 |
| 2-Phenylethyl alcohol | 275.00 |
| Styrene acetate | 20.00 |
| Terpineol | 30.00 |
| Tetrahydrolinalool | 50.00 |
| Cinnamon alcohol | 10.00 |
| Total | 1,000.00 |

Example P3

Perfume Oil Having "White Blossom" Odor (not According to the Invention)

| Components | Parts by weight |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol | 60.00 |
| Ethyllinalool | 40.00 |
| Florol (2-isobutyl-4-methyl-tetrahydro-2H-pyran-4-ol) | 30.00 |
| Globanone ((E/Z)-8-cyclohexadecen-1-one) | 180.00 |
| Hedione (methyl dihydrojasmonate) | 140.00 |
| Hexenyl salicylate, cis-3 | 10.00 |
| Vertocitral (2,4-dimethyl-3-cyclohexencarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one), 10% in DPG | 5.00 |
| Isomuscone (Cyclohexadecanone) | 40.00 |
| Jacinthaflor (2-methyl-4-phenyl-1,3-dioxolan) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| Para-methylkresol, 10% in DPG | 10.00 |
| Nerol | 20.00 |
| Phenylpropyl aldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total | 1,000.00 |

Example P4

Perfume Oil (not According to the Present Invention) Particularly Suitable for Use in Deodorants and Antiperspirants

| Components | Parts by weight |
|---|---|
| 10-Undecenal, 10% in DPG | 2.00 |
| Vertocitral[1] (2,4-dimethyl-3-cyclohexencarboxaldehyde) | 0.50 |
| cis-3-Hexenyl acetate, 10% in DPG | 7.50 |
| Allylamylglycolate[3] | 2.00 |
| Melonal[2] | 0.50 |
| Bergamotte oil | 80.00 |
| Dihydromyrcenol | 90.00 |
| Terpinyl acetate | 40.00 |
| *Litsea cubeba* oil | 2.00 |
| Lemon oil | 50.00 |
| Orange oil | 20.00 |
| Grapefruit oil | 10.00 |
| Lavandin oil abrialis | 10.00 |
| Isobornyl acetate | 3.00 |
| Lysmeral[4] | 10.00 |
| Calone 1951[5] | 2.50 |
| Florhydral[2] | 1.50 |
| Florol[9] | 12.00 |
| Tetrahydrolinalool | 75.00 |
| *Geranium* oil | 5.00 |
| Isodamascone[1] (1-(2,4,4-trimethyl-2-cyclohexen-1-yl)-2-buten-1-one), 10% in DPG | 2.00 |
| Resedafol[1], 10% in DPG [2-(1-propoxyethoxy)ethyl]benzene | 1.00 |
| Methyl dihydrojasmonate (Hedione[9] HC) | 180.00 |
| Jessemal[3] (3-butyl-5-methyl tetrahydropyran-4-yl-acetate) | 4.00 |
| Benzyl salicylate | 10.00 |
| Alpha-isomethylionone | 8.00 |
| Anethole | 3.00 |
| Methyl cedrylketone | 50.00 |
| Iso E Super[3] | 25.00 |
| Ambrocenide[1] ((4aR,5R,7aS,9R)-octahydro-2,2,5,8,8,9a-hexamethyl-4H-4a,9-methano-azuleno(5,6-d)-1,3-dioxol), 1% in DPG | 3.00 |

-continued

| Components | Parts by weight |
|---|---|
| Timberol[1] (1-(2,2,6-trimethylcyclo-hexyl)hexan-3-ol) | 2.00 |
| Patchouli oil | 3.50 |
| Evernyl[2] (methyl-2,4-dihydroxy-3,6-dimethyl benzoate) | 1.60 |
| Labdanum absolue, 20% in DPG | 2.00 |
| Amber Core[6] | 10.00 |
| Ambraketal[2] | 1.50 |
| Hydroxyambran[7] (2-cyclododecylpropanol), 50% in DPG | 5.00 |
| Macrolide[1] (15-cyclopentadecanolide) | 35.00 |
| Globalide[1] (15-pentadec-(11/12)-enolide) | 25.00 |
| Isopropyl myristate (IPM) | Ad 1,000.00 |

Example P5

Perfume Oil Accord Particularly Suitable for Use in Deodorants and Antiperspirants for Freshness Boosting (not According to the Present Invention)

| Components | Parts by weight |
|---|---|
| l-Menthyl methyl ether | 100.00 |
| l-Menthol | 10.00 |
| Linalool | 20.00 |
| Trans-3 hexenyl acetate | 0.25 |
| Cis-3 hexenyl acetate | 0.25 |
| Vertocitral[1] | 1.00 |
| Stemone[2] | 0.50 |
| Styrolyl acetate | 5.00 |
| Cis-3,3,5-trimethyl cyclohexyl acetate | Ad 850.00 |
| Melonal[2] | 0.50 |
| Dihydromyrcenol | 200.00 |
| Orange oil | 35.00 |
| Grapefruit oil | 15.00 |
| Claritone[1] | 1.50 |
| Oxane[9], 10% in DPG | 2.00 |
| Eucalyptus oil globulus | 8.00 |
| Peppermint oil arvensis | 8.00 |
| Borneol | 1.00 |
| Helional[3] | 10.00 |
| Florhydral[2] | 1.00 |
| Tetrahydrolinalool | 80.00 |
| Hedione[9] | 30.00 |
| 2,6-Nonadienol, 10% in IPM | 1.00 |

Example D1

Antiperspirant Spray

To a mixture of suitable carriers comprising 12.5 parts by weight Miglyol 840 Gel B (a mixture of propylene glycol dicaprylate-dicaprate, steralkonium hectorite and propylene carbonate; manufacturer: Sasol), and 46.5 parts by weight silicon oils (cyclomethicon, dimethiconol; manufacturer Dow Corning) 40 parts by weight of aluminum hydrochlorate were added. Once the mixture had homogenized, the following were added:

a) 0.5 parts by weight of 5-cyclohexyl-2-methyl-pentanol of Synthesis Example 2; and b) 0.5 parts by weight of the Perfume oil of Example P4.

From 1 part by weight of the resultant solution and 3 parts by weight of a propellant gas (propane/butane; pressure 2.5 to 2.7 bar) an aerosol spray was produced which was used as an antiperspirant spray on a large number of test subjects to prevent the smell of underarm sweat.

Example D2

Deo Sticks

| Components | A % by weight | B % by weight | C % by weight | D % by weight |
|---|---|---|---|---|
| Sodium stearate | 7.00 | 8.00 | 7.00 | 7.00 |
| Sodium palmitate | 1.00 | — | — | 0.50 |
| 1,2-Propylene glycol | 42.00 | 45.00 | 44.00 | 48.00 |
| 1,2-Butylene glycol | 3.00 | — | 2.00 | — |
| 2-Butyloctanoic acid | — | 0.50 | 0.10 | 0.20 |
| 2-Hexyldecanoic acid | 0.10 | — | — | 0.20 |
| Polyethylenglycol (25) cetearylether | 3.00 | 3.00 | — | — |
| Ethanol | 20.00 | 20.00 | — | — |
| Farnesol | — | 0.25 | 0.50 | — |
| Parabens (mixture of methyl-, ethyl-, propyl-, butyl-, isobutylparaben) | 0.30 | — | 0.40 | — |
| 1,2-hexandiol/1,2-octandiol (1:1) (Symdiol 68) | — | 0.50 | — | 0.50 |
| 1,2-Pentandiol (Hydrolite-5) | 0.50 | — | 2.00 | — |
| (−)-Alpha-Bisabolol, natural | 0.10 | — | — | 0.12 |
| 5-Cyclohexyl-2-methyl-pentanol of Synthesis Example 2 | 0.35 | — | 0.40 | — |
| 5-Cyclohexyl-2-n-propyl-pentanol of Synthesis Example 1.3 | — | 0.40 | — | 0.50 |
| Perfume oil of Example P5 | — | — | 0.45 | — |
| Perfume oil of Example P1 | 0.70 | — | 0.45 | — |
| Perfume oil of Example P3 | — | 0.80 | — | 0.70 |
| Water | To 100 | To 100 | To 100 | To 100 |

Example D3

Transparent Deo-Sticks (Formulations A, B) or Deo-Creme Sticks (Formulations C, D)

| Components | A % by weight | B % by weight | C % by weight | D % by weight |
|---|---|---|---|---|
| Aluminum zirconium tetrahydrochlorate - glycin Komplex | 25.00 | 20.00 | 25.00 | 20.00 |
| Dimethicon (10 cst) | — | — | 5.00 | 5.00 |
| Cyclopentasiloxane | — | 0.50 | 1.00 | 0.50 |
| Petrolatum | 5.00 | 4.70 | 5.00 | 5.00 |
| Ozokerite | 1.00 | 1.50 | — | — |
| Stearyl alcohol | 12.00 | 12.00 | — | — |
| 2-Butyloctanoic acid | 0.50 | — | 0.50 | — |
| Wax | — | — | 1.25 | 1.25 |
| PPG-14 butyl ether | 9.00 | 9.00 | — | — |
| Hardened rapeseed oil | — | — | 5.00 | 5.00 |
| Silicon dioxide | — | — | 1.00 | — |
| Farnesol | 0.25 | — | 0.25 | — |
| Paraffin oil | 0.50 | 0.50 | — | — |
| Hydrated castor oil (castor wax) | 3.50 | 3.50 | — | — |
| Talc | 4.00 | 4.00 | — | — |
| Behenyl alcohol | 0.20 | 0.20 | — | — |
| d-Panthenyl triacetate | 1.00 | 1.00 | — | — |
| Preservative (BHT) | 0.10 | 0.10 | 0.12 | — |
| Phenoxy ethanol | — | 0.15 | — | 0.50 |

| Components | A % by weight | B % by weight | C % by weight | D % by weight |
|---|---|---|---|---|
| 5-Cyclohexyl-2-methyl-pentanol of Synthesis Example 2 | 0.50 | — | 0.45 | — |
| 5-Cyclohexyl-3-methyl-pentanol of Synthesis Example 3 | — | 0.60 | — | 0.45 |
| Perfume oil of Example P4 | — | 0.15 | — | — |
| Perfume oil of Example P2 | 0.80 | 0.55 | — | 0.50 |
| Perfume oil of Example P3 | — | — | 0.80 | 0.25 |
| Water | To 100 | To 100 | To 100 | To 100 |

Example D4

Roll-on Antiperspirant

| Components | % by weight | % by weight |
|---|---|---|
| Caprylyl Trimethicon (SilCare TM Silicone 31 M 50) | 0.30 | 0.30 |
| Steareth-20 (GENAPOL TM HS 200) | 3.00 | 3.00 |
| Steareth-2 (GENAPOL TM HS 020) | 1.50 | 1.50 |
| Dicaprylyl ether (Cetiol TM OE) | 2.00 | 2.00 |
| Coco caprylate/caprate (Cetiol TM LC) | 2.00 | 2.00 |
| Glycerine | 2.00 | 2.00 |
| Glyceryl stearate (Cutina TM GMS) | 2.00 | 2.00 |
| Octyldodecanol (Eutanol TM G) | 1.00 | 1.00 |
| Stearyl alcohol | 2.50 | 2.50 |
| Aluminum hydrochloride according to example 1 of EP 1321431 | 10.00 | 10.00 |
| Avocado extract Persea gratissima | 0.30 | 0.20 |
| Chamomile extract | 0.10 | — |
| 5-Cyclohexyl-2-methyl-pentanol of Synthesis Example 2 | 0.30 | 0.60 |
| Perfume oil of Example P1 | 0.85 | — |
| Perfume oil of Example P5 | — | 0.30 |
| Perfume oil of Example P4 | — | 0.75 |
| Water | To 100 | To 100 |

Example D5

Antiperspirant Stick

| Components | % by weight | % by weight | % by weight |
|---|---|---|---|
| Phenyl Trimethicon (SilCare TM Silicone 15 M 50) | 13.50 | 13.50 | 13.50 |
| Cetearyl alcohol | To 100 | To 100 | To 100 |
| Cetiol CC (dicaprylyl carbonate) | 13.50 | 13.50 | 13.50 |
| Stearic acid | 3.50 | 3.50 | 3.50 |
| PEG-40-hydrated castor oil (Emulsogen TM HCO 040) | 4.10 | 4.10 | 4.10 |
| PEG-8 distearate (Cithrol 4 DS) | 4.10 | 4.10 | 4.10 |
| Petrolatum | 6.90 | 6.90 | 6.90 |
| Aluminum hydrochlorate | 13.80 | 13.80 | 13.80 |
| Aluminum zirconium trichlorohydrex gly | 20.00 | 19.50 | 20.00 |
| Neo Helopan Hydro (phenylbenzimidazole sulphonic acid, Symrise) | 2.00 | — | 3.50 |
| 2,2-Dimethyl-3-phenylpropanol (muguet alcohol) | — | 0.25 | — |
| Ethylhexylglycerin (octoxyglycerin) | — | 0.30 | 0.20 |
| 1,1-Dimethyl-3-phenylpropanol | — | 0.25 | 0.10 |
| 5-Cyclohexyl-2,4-dimethyl-pentanol of Synthesis Example 5 | 0.20 | — | 0.55 |
| 5-Cyclohexyl-2-methyl-pentanol of Synthesis Example 2 | 0.35 | 0.50 | — |
| Perfume oil of Example P1 | 0.75 | 0.30 | — |
| Perfume oil of Example P2 | — | 0.40 | 0.95 |

Example D6

Antiperspirant Spray

| Components | % by weight | % by weight | % by weight |
|---|---|---|---|
| Glyceryl stearate | 2.50 | 2.50 | 2.50 |
| Cetearyl alcohol | 1.00 | 1.00 | 1.00 |
| Ceteareth-20 | 2.50 | 2.50 | 2.50 |
| Ceteareth-12 | 1.00 | 1.00 | 1.00 |
| Dicaprylyl ether | 5.00 | 5.00 | 5.00 |
| Coco caprylate/caprate | 5.00 | 5.00 | 5.00 |
| Caffeine | 0.25 | 0.25 | 0.25 |
| Phenoxy ethanol | 0.25 | 0.25 | 0.25 |
| Parabens (mixture of methyl-, ethyl-, propyl-, butyl-, isobutylparaben) | 0.25 | 0.25 | 0.25 |
| 1,2-Pentandiol (Hydrolite-5) | 2.00 | 1.00 | 1.20 |
| Aluminum hydrochlorate | 8.00 | 8.00 | 8.00 |
| Neo Heliopan AP (disodium phenyl dibenzimidazole tetrasulfonate, Symrise) | 1.00 | — | 1.00 |
| 4-Methyl-4-phenyl-2-pentanol (Vetikol) | — | 0.10 | 0.10 |
| Ethylhexylglycerin (octoxyglycerin) | — | 0.30 | 0.50 |
| Perfume oil of Example P5 | 0.25 | 0.30 | — |
| Perfume oil of Example P1 | 0.60 | — | — |
| Perfume oil of Example P4 | — | 0.50 | 1.00 |
| 5-(4-Isopropylcyclohexyl)-2-methyl-1-pentanol of Synthesis Example 4 | — | 0.50 | — |
| 5-Cyclohexyl-2-methyl-pentanol of Synthesis Example 2 | 0.40 | — | 0.50 |
| Water | To 100 | To 100 | To 100 |

Example D7

Aerosol Spray

| Components | % by weight | % by weight | % by weight |
|---|---|---|---|
| Octyldodecanol | 0.50 | — | 0.50 |
| Phenoxy ethanol | — | — | 0.30 |
| 1,2-Pentandiol (Hydrolite-5) | 1.00 | 1.00 | 0.50 |
| 1,2-Hexandiol | 0.25 | 0.15 | — |
| 1,2-Octandiol | 0.25 | 0.25 | — |

-continued

| Components | % by weight | % by weight | % by weight |
|---|---|---|---|
| Farnesol | 0.25 | — | 0.25 |
| L-menthyl lactate (Frescolat ML, Symrise) | 0.25 | 0.40 | 0.60 |
| 1,1-Dimethyl-3-phenylpropanol | 0.30 | — | 0.10 |
| Ethylhexylglycerin (octoxyglycerin) | — | 0.30 | 0.50 |
| 5-Cyclohexyl-2-methyl-pentanol of Synthesis Example 2 | 0.50 | 0.30 | — |
| 5-Cyclohexyl-3-methyl-pentanol of Synthesis Example 3 | — | 0.30 | 0.50 |
| Perfume oil of Example P4 | 0.90 | 1.05 | — |
| Perfume oil of Example P3 | — | — | 0.80 |
| Ethanol | To 100 | To 100 | To 100 |

The liquid mixture obtained following the mixing together of the stated components was filled with a propane-butane mixture (2:7=in the ratio 2:3) in an aerosol container

Example D8

Pump Spray

| Components | % by weight | % by weight | % by weight |
|---|---|---|---|
| PEG-40 hydrated castor oil | 2.00 | 2.00 | 2.00 |
| Glycerine | 1.00 | 1.00 | 1.00 |
| 1,2-Pentandiol (Hydrolite-5) | — | 1.00 | 2.00 |
| 1,2-Hexandiol | 0.25 | 0.15 | — |
| 1,2-Octandiol | 0.25 | 0.15 | — |
| Anis alcohol | 0.15 | 0.10 | 0.25 |
| 2-Methyl-4-phenyl-2-butanol | 0.40 | 0.50 | — |
| Ethylhexylglycerin (octoxyglycerin) | — | — | 0.40 |
| 5-Cyclohexyl-2-methyl-pentanol of Synthesis Example 2 | 0.50 | — | 0.50 |
| 5-Cyclohexyl-2,4-dimethyl-pentanol of Synthesis Example 5 | — | 0.50 | — |
| Perfume oil of Example P4 | 1.00 | 0.90 | — |
| Perfume oil of Example P3 | — | 0.15 | 0.90 |
| Water | To 100 | To 100 | To 100 |

Example D9

Roll-on Gel

| Components | % by weight | % by weight | % by weight |
|---|---|---|---|
| PEG-40 hydrated castor oil | 2.00 | 2.00 | 2.00 |
| 1,3-Butylene glycol | 2.00 | 2.00 | 2.00 |
| Hydroxyethylcellulose | 0.50 | 0.50 | 0.50 |
| 1,2-Pentandiol (Hydrolite-5) | — | 1.00 | 2.00 |
| 1,2-Hexandiol | 0.25 | 0.15 | — |
| 1,2-Octandiol | 0.25 | — | 0.25 |
| L-Menthyl lactate (Frescolat ® ML, Symrise) | 0.25 | — | 0.25 |
| Menthone glycerine acetal (Frescolat ® MGA, Symrise) | — | 0.50 | 0.25 |
| Phenoxy ethanol | 0.15 | 0.10 | 0.25 |

-continued

| Components | % by weight | % by weight | % by weight |
|---|---|---|---|
| 1,1-Dimethyl-3-phenylpropanol | — | 0.15 | 0.10 |
| Ethylhexylglycerin (octoxyglycerin) | 0.50 | 0.40 | — |
| 5-Cyclohexyl-2-methyl-pentanol of Synthesis Example 2 | 0.30 | — | 0.45 |
| 5-Cyclohexyl-2-n-propyl-pentanol of Synthesis Example 1.3 | — | 0.40 | — |
| Perfume oil of Example P1 | 1.00 | 1.10 | — |
| Perfume oil of Example P2 | — | — | 1.00 |
| Water | To 100 | To 100 | To 100 |

Example D10

Roll-on Emulsion

| Components | % by weight | % by weight | % by weight |
|---|---|---|---|
| Triceteareth-4 phosphate | 0.30 | 0.30 | 0.30 |
| Octyldodecanol | 2.00 | 2.00 | 2.00 |
| $C_{12-15}$-alkylbenzoate | 2.00 | 2.00 | 2.00 |
| $C_{10-30}$-alkyl acrylate | 0.15 | 0.15 | 0.15 |
| 1,2-Hexandiol/1,2-octandiol (1:1) (Symdiol 68) | — | 0.50 | 0.25 |
| Phenoxy ethanol | 0.25 | 0.25 | — |
| Parabens | 0.25 | — | 0.20 |
| 4-Methyl-4-phenyl-2-pentanol (Vetikol) | 0.10 | — | 0.10 |
| Ethylhexylglycerin (octoxyglycerin) | 0.50 | — | — |
| 5-Cyclohexyl-2-methyl-pentanol of Synthesis Example 2 | 0.35 | — | 0.45 |
| 5-Cyclohexyl-2-n-propyl-pentanol of Synthesis Example 1.3 | — | 0.40 | — |
| Perfume oil of Example P1 | — | 0.70 | 1.00 |
| Perfume oil of Example P3 | 1.00 | — | — |
| Perfume oil of Example P5 | — | 0.20 | — |
| Water | To 100 | To 100 | To 100 |

Example D11

Wax Stick

| Components | % by weight | % by weight | % by weight |
|---|---|---|---|
| Hydrated castor oil | 5.00 | 5.00 | 5.00 |
| Beeswax | 6.00 | 6.00 | 6.00 |
| $C_{12-15}$-alkylbenzoate | 17.00 | 17.00 | 17.00 |
| Ceresin | 30.00 | 30.00 | 30.00 |
| Neo Heliopan AV (ethylhexyl methoxycinnamate, Symrise) | 1.00 | 2.00 | — |
| Neo Heliopan 357 (butyl methoxydibenzoylmethane, Symrise) | 1.00 | — | 2.50 |
| 1,2-Hexandiol/1,2-octandiol (1:1) (Symdiol 68) | — | 0.50 | 0.25 |
| Phenoxy ethanol | 0.50 | — | — |
| Parabens | — | — | 0.25 |
| 1,1-Dimethyl-3-phenylpropanol | 0.20 | — | 0.10 |

-continued

| Components | % by weight | % by weight | % by weight |
|---|---|---|---|
| 2-Methyl-4-phenyl-2-butanol | — | 0.50 | — |
| 2,2-Dimethyl-3-phenylpropanol (muguet alcohol) | 0.30 | — | 0.35 |
| 5-Cyclohexyl-2-methyl-pentanol of Synthesis Example 2 | 0.60 | 0.40 | — |
| 5-Cyclohexyl-2-n-propyl-pentanol of Synthesis Example 1.3 | — | — | 0.50 |
| Perfume oil of Example P1 | 1.20 | — | 0.50 |
| Perfume oil of Example P3 | — | 1.10 | 0.70 |
| Octyldodecanol | To 100 | To 100 | To 100 |

Example D12

Deo Atomizer

| Components | % by weight | % by weight | % by weight |
|---|---|---|---|
| PEG-40 hydrated castor oil | 3.00 | 3.00 | 3.00 |
| Ethylhexylglycerin (octoxyglycerin) | 0.80 | 0.80 | 1.00 |
| Ethanol | 40.00 | 40.00 | 40.00 |
| Citrate buffer | 0.50 | 0.50 | 0.50 |
| 1,2-Hexandiol/1,2-octandiol (1:1) | — | 0.25 | 0.25 |
| Phenoxy ethanol | 0.25 | 0.25 | — |
| Triclosan ® (5-chloro-2-(2,4-dichlorphenoxy)phenol) | 0.25 | — | 0.20 |
| 2-Benzylheptan-1-ol (Jasmol) | — | 0.15 | 0.15 |
| 1,1-Dimethyl-3-phenylpropanol | 0.30 | 0.40 | 0.50 |
| 5-Cyclohexyl-2-methyl-pentanol of Synthesis Example 2 | 0.30 | 0.50 | — |
| 5-Cyclohexyl-3-methyl-pentanol of Synthesis Example 3 | — | — | 0.40 |
| Perfume oil of Example P2 | 0.90 | — | 0.90 |
| Perfume oil of Example P4 | — | 1.05 | — |
| Water | To 100 | To 100 | To 100 |

Example D13

Roll-on

| Components | % by weight | % by weight | % by weight |
|---|---|---|---|
| Hydroxyethylcellulose | 0.50 | 0.50 | 0.50 |
| Ethylhexylglycerin (octoxyglycerin) | 1.00 | 0.80 | 1.00 |
| Ethanol | 45.00 | 45.00 | 40.00 |
| Aluminum hydrochlorate | 15.00 | 15.00 | 20.00 |
| 1,2-Hexandiol/1,2-octandiol (1:1) | — | 0.25 | 0.25 |
| Phenoxy ethanol | 0.25 | 0.25 | — |
| Parabens | 0.25 | — | 0.20 |
| 3-Methyl-6-phenyl-2-hexanol | 0.40 | 0.15 | 0.20 |
| 5-Cyclohexyl-2-methyl-pentanol of Synthesis Example 2 | 0.45 | 0.50 | — |
| 5-Cyclohexyl-2-n-propyl-pentanol of Synthesis Example 1.3 | — | — | 0.40 |
| Perfume oil of Example P1 | 0.65 | — | 0.80 |
| Perfume oil of Example P4 | — | 1.00 | — |
| Perfume oil of Example P5 | 0.25 | — | 0.10 |
| Water | To 100 | To 100 | To 100 |

Example D14

Emulsion Roll-on

| Components | % by weight | % by weight | % by weight |
|---|---|---|---|
| PEG-40 stearate | 5.00 | 5.00 | 5.00 |
| Ethylhexylglycerin (octoxyglycerin) | 1.00 | 0.80 | 1.00 |
| Cetyl alcohol | 2.00 | 2.00 | 2.00 |
| Mineral oil | 2.00 | 2.00 | 2.00 |
| Aluminum hydrochlorate | 15.00 | 15.00 | 15.00 |
| Polysorbate 80 | 1.00 | 1.00 | 1.00 |
| Glycerine | 1.50 | 1.50 | 1.50 |
| Mg-aluminum silicate | 0.80 | 0.80 | 0.80 |
| 1,2-Pentandiol (Hydrolite-5) | — | 0.50 | 1.00 |
| 2-Benzylheptan-1-ol (Jasmol) | — | 0.25 | — |
| 2-Methyl-4-phenylbutan-2-ol | 0.25 | — | 0.40 |
| 5-Cyclohexyl-2-methyl-pentanol of Synthesis Example 2 | 0.30 | — | 0.15 |
| 5-Cyclohexyl-2-n-propyl-pentanol of Synthesis Example 1.3 | — | 0.40 | 0.20 |
| Perfume oil of Example P1 | 0.95 | — | 1.10 |
| Perfume oil of Example P3 | — | 1.00 | — |
| Water | To 100 | To 100 | To 100 |

Example D15

Roll-on

| Components | % by weight | % by weight | % by weight |
|---|---|---|---|
| Steareth-2 | 2.00 | 2.00 | 2.00 |
| Steareth-21 | 5.00 | 5.00 | 5.00 |
| Ethylhexylglycerin (octoxyglycerin) | 1.00 | 0.80 | 1.00 |
| Cetearyl alcohol | 0.50 | 0.50 | 0.50 |
| 1,2-Pentandiol (Hydrolite-5) | — | 0.50 | 1.00 |
| L-Menthylmethylether | — | 0.10 | 0.15 |
| 5-Cyclohexyl-2-methyl-pentanol of Synthesis Example 2 | 0.30 | — | — |
| 5-Cyclohexyl-2,4-dimethyl-pentanol of Synthesis Example 5 | — | 0.50 | — |
| 5-(p-Tert.-butylcyclohexyl)-2-methyl-1-pentanol of Synthesis Example 4.1 | — | — | 0.40 |
| Perfume oil of Example P4 | 1.00 | 1.00 | 1.00 |
| Water | To 100 | To 100 | To 100 |

Example D16

Antiperspirant Aerosol

| Components | % by weight | % by weight | % by weight |
| --- | --- | --- | --- |
| Silicone | 13.00 | 13.00 | 13.00 |
| Ethylhexylglycerin (octoxyglycerin) | 0.80 | 0.80 | 1.00 |
| Ethanol | 0.80 | 0.80 | 0.80 |
| Quaternium-18 hectorite | 0.80 | 0.80 | 0.80 |
| Aluminum hydrochlorate, powder | 10.00 | 10.00 | 10.00 |
| 1,2-Hexandiol/1,2-octandiol (1:1) (Symdiol 68) | 0.50 | 0.25 | 0.40 |
| 5-Cyclohexyl-2-methyl-pentanol of Synthesis Example 2 | 0.30 | — | — |
| 5-Cyclohexyl-3-methyl-pentanol of Synthesis Example 3 | — | 0.40 | — |
| 5-Cyclohexyl-2,4-dimethyl-pentanol of Synthesis Example 5 | — | — | 0.40 |
| Perfume oil of Example P1 | 1.25 | 1.10 | 0.60 |
| Perfume oil of Example P2 | — | — | 0.50 |
| Water | To 100 | To 100 | To 100 |

Quaternium-18 hectorite (INCI-name; CAS#: 71011-27-3):

quaternary ammonium compounds, bis(hydrated tallow-alkyl)dimethyl-, chloride, compounds with hectorite

Example D17

Suspensions Roll-on

| Components | % by weight | % by weight | % by weight |
| --- | --- | --- | --- |
| Silicone | To 100 | To 100 | To 100 |
| Ethylhexylglycerin (octoxyglycerin) | 1.00 | 1.00 | 1.00 |
| Quaternium-18 hectorite | 13.00 | 13.20 | 13.70 |
| Aluminum hydrochlorate, powder | 21.00 | 20.00 | 20.00 |
| 4-Methyl-4-phenyl-2-pentanol (Vetikol) | 0.30 | — | 0.50 |
| 5-Cyclohexyl-2-methyl-pentanol of Synthesis Example 2 | 0.25 | 0.40 | — |
| 5-Cyclohexyl-3-methyl-pentanol of Synthesis Example 3 | 0.15 | — | 0.15 |
| 5-Cyclohexyl-2,4-dimethyl-pentanol of Synthesis Example 5 | — | — | 0.25 |
| Perfume oil of Example P3 | 1.00 | 0.60 | 1.00 |
| Perfume oil of Example P4 | — | 0.50 | — |

Example D18

Suspension Stick

| Components | % by weight | % by weight | % by weight |
| --- | --- | --- | --- |
| Stearyl alcohol | 20.00 | 20.00 | 20.00 |
| Cyclomethicone | To 100 | To 100 | To 100 |
| PPG-14 butyl ether | 2.00 | 2.00 | 2.00 |
| Hydrated castor oil | 1.00 | 1.00 | 1.00 |
| Talc | 2.00 | 2.00 | 2.00 |
| Aluminum hydrochlorate, powder | 20.00 | 20.00 | 20.00 |
| Triclosan ® (5-chloro-2-(2,4-dichlorphenoxy)phenol) | 0.30 | — | 0.30 |
| Ethylhexylglycerin (octoxyglycerin) | 0.50 | 0.80 | 0.50 |
| Anis alcohol | — | — | 0.15 |
| 5-Cyclohexyl-2-methyl-pentanol of Synthesis Example 2 | — | — | 0.35 |
| 5-Cyclohexyl-3-methyl-pentanol of Synthesis Example 3 | — | 0.35 | — |
| 2,4-Dimethyl-5-(4-isopropyl-cyclohexyl)-1-pentanol of Synthesis Example 6 | 0.40 | — | — |
| Perfume oil of Example P3 | 0.95 | — | 1.00 |
| Perfume oil of Example P4 | — | 0.90 | — |

Example D19

Antiperspirant Formulations

| Components | % by weight | % by weight | % by weight |
| --- | --- | --- | --- |
| Reach AZP-908 SUF | 24.00 | 22.00 | 20.00 |
| Cyclomethicone (Pentamer) | To 100 | To 100 | To 100 |
| Polydecene (Silkflo 364 NF) | 17.50 | 20.00 | 20.00 |
| Neo Helipan OS (ethylhexyl salicytate, Symrise) | 2.50 | 1.00 | — |
| L-Menthyl lactate (Frescolat ML, Symrise) | 0.25 | — | 0.50 |
| Polyethylene | 3.00 | 3.00 | 3.00 |
| Hydrated castor oil | 2.00 | 2.00 | 2.00 |
| Promyristyl PM-3 | 7.00 | 7.00 | 7.00 |
| PEG-8 distearate | 3.00 | 3.00 | 3.00 |
| Silicon dioxide (Cab-O-Sil M-5) | 1.00 | 1.00 | 1.00 |
| Stearyl alcohol | 15.00 | 10.00 | 15.00 |
| Octyldodecanol | — | 8.00 | — |
| 5-Cyclohexyl-2-methyl-pentanol of Synthesis Example 2 | 0.25 | 0.40 | — |
| 5-Cyclohexyl-3-methyl-pentanol of Synthesis Example 3 | 0.20 | — | 0.40 |
| Perfume oil of Example P1 | 0.80 | 0.80 | — |
| Perfume oil of Example P4 | — | — | 0.70 |
| Perfume oil of Example P5 | 0.20 | 0.20 | 0.30 |

Reach AZP-908 SUF: activated aluminum zirconium tetrachlorohydrex glycine-complex, a product of Reheis Inc.

Example D20

Impregnation Medium for Deo-Cloths

| Components | % by weight | % by weight | % by weight |
|---|---|---|---|
| PEG-40 hydrated castor oil | 3.00 | 3.00 | 3.00 |
| Octoxyglycerin | 1.00 | 0.80 | 0.90 |
| 2-Methyl-4-phenylbutan-2-ol | 0.80 | 0.60 | 0.40 |
| Citrate buffer | 0.50 | 0.50 | 0.50 |
| Ethanol | 40.00 | 40.00 | 40.00 |
| 5-Cyclohexyl-2-methyl-pentanol of Synthesis Example 2 | 0.30 | — | 0.20 |
| 5-Cyclohexyl-2-n-propyl-pentanol of Synthesis Example 1.3 | — | 0.40 | 0.10 |
| Perfume oil of Example P1 | 0.50 | — | — |
| Perfume oil of Example P2 | — | 0.60 | — |
| Perfume oil of Example P4 | — | — | 0.50 |
| Water | To 100 | To 100 | To 100 |

Example D21

PIT Emulsion

| Components | % by weight | % by weight | % by weight |
|---|---|---|---|
| Glyceryl stearate, ceteareth-20, ceteareth-10, cetearyl alcohol, cetyl palmitate | 4.50 | 4.50 | 4.50 |
| Octoxyglycerin | 1.00 | 0.80 | 0.90 |
| Ceteareth-20 | 1.00 | 1.00 | 1.00 |
| Dicaprylyl ether | 5.00 | 5.00 | 5.00 |
| Dioctylcyclohexane | 5.00 | 5.00 | 5.00 |
| Aluminum hydrochlorate | 5.00 | 5.00 | 5.00 |
| 5-Cyclohexyl-2-methyl-pentanol of Synthesis Example 2 | 0.27 | — | 0.40 |
| 5-Cyclohexyl-2-n-propyl-pentanol of Synthesis Example 1.3 | 0.05 | 0.30 | — |
| Perfume oil of Example P2 | 0.95 | — | — |
| Perfume oil of Example P4 | — | 1.00 | 1.20 |
| Water | To 100 | To 100 | To 100 |

Example D22

Micro-Emulsion

| Components | % by weight | % by weight | % by weight |
|---|---|---|---|
| Glycerine isostearate | 1.80 | 2.00 | 1.80 |
| Octoxyglycerin | 1.00 | 0.80 | 0.90 |
| Ceteareth-15 | 5.20 | 5.50 | 5.00 |
| Isotridecylisononanoate | 3.30 | 3.50 | 3.80 |
| Cyclomethicon | 6.60 | 6.40 | 6.20 |
| 5-Cyclohexyl-2-methyl-pentanol of Synthesis Example 2 | 0.25 | — | 0.40 |
| 5-Cyclohexyl-3-methyl-pentanol of Synthesis Example 3 | 0.10 | 0.30 | — |
| Perfume oil of Example P1 | 0.95 | — | — |
| Perfume oil of Example P3 | — | 100 | 1.15 |
| Water | To 100 | To 100 | To 100 |

Example D23

Micro-Emulsion Gel

| Components | % by weight | % by weight | % by weight |
|---|---|---|---|
| Glycerine isostearate | 1.80 | 2.00 | 1.80 |
| Octoxyglycerin | 1.00 | 0.80 | 0.90 |
| Ceteareth-15 | 5.20 | 5.00 | 5.50 |
| PEG-150 distearate | 1.00 | 1.00 | 1.00 |
| Aluminum hydrochlorate | 5.00 | 5.00 | 5.00 |
| Isotridecylisononanoate | 3.30 | 3.50 | 3.80 |
| Cyclomethicon | 6.60 | 6.40 | 6.20 |
| 5-Cyclohexyl-2-methyl-pentanol of Synthesis Example 2 | 0.20 | — | 0.35 |
| 5-Cyclohexyl-3-methyl-pentanol of Synthesis Example 3 | 0.10 | 0.30 | — |
| Perfume oil of Example P2 | 0.95 | — | — |
| Perfume oil of Example P3 | — | 1.00 | 1.15 |
| Water | To 100 | To 100 | To 100 |

Example D24

Deo-Stick

| Components | A<br>% by weight | B<br>% by weight | C<br>% by weight |
|---|---|---|---|
| Sodium stearate | 8.00 | 8.00 | 8.00 |
| PPG-3 myristyl ether | 70.00 | 70.00 | 70.00 |
| 1,2-Propylene glycol | 10.00 | 10.00 | 10.00 |
| 1,1-Dimethyl-3-phenylpropanol | 0.50 | — | 0.30 |
| 2-Butyloctanoic acid | — | 0.20 | 0.10 |
| 5-Cyclohexyl-2-methyl-pentanol of Synthesis Example 2 | 0.45 | — | 0.20 |
| 5-Cyclohexyl-3-methyl-pentanol of Synthesis Example 3 | — | 0.55 | 0.35 |
| Perfume oil of Example P2 | 1.20 | — | — |
| Perfume oil of Example P3 | — | 1.25 | 0.80 |
| Perfume oil of Example P5 | — | — | 0.30 |
| Water | To 100 | To 100 | To 100 |

Example D25

Antiperspirant Stick

| Components | % by weight | % by weight | % by weight |
|---|---|---|---|
| Octyldodecanol | 8.00 | 7.00 | 8.50 |
| C20-40 pareth 10 | 0.50 | 0.50 | 0.50 |
| C20-40 pareth 40 | 1.50 | 1.50 | 1.50 |
| Stearyl alcohol | 4.00 | 4.00 | 3.00 |
| Hydrated castor oil | 2.00 | 2.00 | 2.00 |
| Octylisononanoate | 9.00 | 9.50 | 8.50 |
| Polydecene (Silkflo 364 NF) | 9.00 | 9.50 | 8.50 |
| PEG-14 butyl ether | 4.50 | 4.80 | 5.00 |
| Paraffin oil | 5.00 | 4.80 | 4.50 |
| Reach AZP-908 SUF (see example 24) | 24.00 | 24.00 | 24.00 |
| Tween-80 | 0.80 | 0.80 | 0.80 |
| Cyclomethicon | To 100 | To 100 | To 100 |
| Bentone gel VS-5 PC | 0.50 | 0.50 | 0.50 |
| Bishydrated tallow glyceride | 8.00 | 5.00 | — |
| 5-Cyclohexyl-2-methyl-pentanol of Synthesis Example 2 | 0.50 | — | 0.30 |
| 5-Cyclohexyl-2-n-propyl-pentanol of Synthesis Example 1.3 | — | 0.55 | 0.25 |
| Perfume oil of Example P1 | 1.20 | — | — |
| Perfume oil of Example P4 | — | 1.25 | 1.00 |
| Water | To 100 | To 100 | To 100 |

Example D26

Hair Créme

| Components | % by weight | % by weight | % by weight |
|---|---|---|---|
| Vaseline | 4.00 | 4.00 | 4.00 |
| Cetearyl alcohol | 4.00 | 4.00 | 4.00 |
| PEG-40 hydrated castor oil | 2.00 | 2.00 | 2.00 |
| Isopropylpalmitate | 5.00 | 5.00 | 5.00 |
| Citric acid | 5.00 | 5.00 | 5.00 |
| Phenoxy ethanol | 0.30 | 0.60 | 0.70 |
| BHT | 0.10 | — | — |
| 5-Cyclohexyl-2-methyl-pentanol of Synthesis Example 2 | 0.50 | — | 0.25 |
| 5-Cyclohexyl-3-methyl-pentanol of Synthesis Example 3 | — | 0.60 | 0.35 |
| Perfume oil of Example P2 | 1.20 | — | — |
| Perfume oil of Example P4 | — | 1.25 | 0.80 |
| Perfume oil of Example P5 | — | — | 0.30 |
| Water | To 100 | To 100 | To 100 |

Example D27

Foot Créme

| Components | % by weight | % by weight | % by weight |
|---|---|---|---|
| Soluan 5 | 2.00 | 2.00 | 2.00 |
| Methylsalicylate | 1.00 | 1.00 | 1.00 |
| Coco caprylate/caprate | 10.00 | 10.00 | 10.00 |
| Stearic acid | 5.00 | 5.00 | 5.00 |
| Cetyl alcohol | 1.00 | 1.00 | 1.00 |
| Glycerine | 2.00 | 2.00 | 2.00 |
| Dimethicon | 1.00 | 1.00 | 1.00 |
| Carbopol 984 | 0.50 | 0.50 | 0.50 |
| Triethanolamine | 1.50 | 1.50 | 1.50 |
| Phenoxy ethanol | 0.50 | — | 0.30 |
| 1,2-Pentandiol (Hydrolite-5, Symrise) | 0.50 | 2.00 | 1.50 |
| 5-Cyclohexyl-2-methyl-pentanol of Synthesis Example 2 | 0.30 | — | 0.15 |
| 5-Cyclohexyl-2-n-propyl-pentanol of Synthesis Example 1.3 | — | 0.30 | 0.20 |
| Perfume oil of Example P1 | — | 1.00 | 0.60 |
| Perfume oil of Example P4 | 1.20 | — | 0.60 |
| Water | To 100 | To 100 | To 100 |

Example D28

Syndet Soap

| Components | % by weight | % by weight | % by weight |
|---|---|---|---|
| Sodium lauryl sulphate | 30.00 | 30.00 | 30.00 |
| Sodium sulphosuccinate | 10.00 | 10.00 | 10.00 |
| Potassium cocoyl hydrolyzed collagen | 2.00 | 2.00 | 2.00 |
| Dimethicon copolyol | 2.00 | 2.00 | 2.00 |
| Paraffin | 2.00 | 2.00 | 2.00 |
| Maize starch | 10.00 | 10.00 | 10.00 |
| Talcum | 10.00 | 10.00 | 10.00 |
| Glycerine | 3.00 | 3.00 | 3.00 |
| Phenoxy ethanol | 0.50 | 0.50 | 0.50 |
| 5-Cyclohexyl-2-methyl-pentanol of Synthesis Example 2 | 0.60 | — | — |
| 5-Cyclohexyl-2-n-propyl-pentanol of Synthesis Example 1.3 | — | 0.60 | — |
| 5-Cyclohexyl-3-methyl-pentanol of Synthesis Example 3 | — | — | 0.60 |
| Perfume oil of Example P2 | 1.40 | — | 0.70 |
| Perfume oil of Example P4 | — | 1.20 | 0.50 |
| Water | To 100 | To 100 | To 100 |

Example D29

O/W Lotion

| Components | % by weight | % by weight | % by weight |
|---|---|---|---|
| Paraffin oil | 5.00 | 5.00 | 5.00 |
| Isopropylpalmitate | 5.00 | 5.00 | 5.00 |
| Cetyl alcohol | 2.00 | 2.00 | 2.00 |
| Beeswax | 2.00 | 2.00 | 2.00 |
| Ceteareth-20 | 2.00 | 2.00 | 2.00 |
| PEG-20-glyceryl stearate | 1.50 | 1.50 | 1.50 |
| Glycerine | 3.00 | 3.00 | 3.00 |
| Phenoxy ethanol | 0.50 | 0.50 | — |
| Parabens (mixture of methyl-, ethyl-, propyl-, butyl-, isobutylparaben) | — | — | 0.30 |
| 5-Cyclohexyl-2-methyl-pentanol of Synthesis Example 2 | 0.40 | — | — |
| 5-Cyclohexyl-2-n-propyl-pentanol of Synthesis Example 1.3 | — | 0.30 | — |
| 5-Cyclohexyl-3-methyl-pentanol of Synthesis Example 3 | — | — | 0.40 |
| Perfume oil of Example P2 | 1.00 | — | 0.50 |
| Perfume oil of Example P3 | — | 0.95 | 0.50 |
| Water | To 100 | To 100 | To 100 |

Example D30

Hair Conditioner with UV Protection

| Components | INCI Name | % by weight | % by weight |
|---|---|---|---|
| Lanette O | Cetearyl Alcohol | 4.00 | 4.00 |
| Dragoxat 89 | Ethylhexyl Isononanoate | 4.00 | 4.00 |
| Emulsiphos | Potassium Cetyl Phosphate, Hydrogenated Palm Glycerides | 0.50 | 0.50 |
| Natrosol 250 HR | Hydroxyethylcellulose | 0.25 | 0.25 |
| Neo Heliopan Hydro | Phenylbenzimidazole Sulphonic Acid | 2.00 | 2.00 |
| L-Arginin | Arginine | 1.20 | 1.20 |
| Benzophenone-4 | Benzophenone-4 | 0.50 | 0.50 |
| Neo Heliopan AP | Disodium Phenyl Dibenzimidazole Tetrasulfonate | 0.50 | 1.00 |
| Edeta BD | Disodium EDTA | 0.05 | 0.05 |
| Dragocide Liquid | Phenoxyethanol (and) Methylparaben (and) Butyparaben (and) Ethyparaben (and) Propylparaben | 0.80 | 0.80 |
| Dow Corning 949 Cationic Emulsion | Amodimethicone, Cetrimonium Chloride, Trideceth-12 | 2.00 | 2.00 |
| Dow Corning 5200 | Laurylmethicone Copolyol | 0.50 | 0.50 |
| 5-Cyclohexyl-2-methyl-pentanol of Synthesis Example 2 | | 0.25 | — |
| 5-Cyclohexyl-2-n-propyl-pentanol of Synthesis Example 1.3 | | — | 0.25 |
| Perfume oil of Example P1 | Parfum | 0.75 | — |
| Perfume oil of Example P2 | Parfum | — | 0.90 |
| Water | Water (Aqua) | To 100 | To 100 |

Example D31

Hair Conditioner with UV Protection

| Components | INCI Name | % by weight | % by weight |
|---|---|---|---|
| Renex PEG 6000 | PEG-150 | 2.50 | 2.50 |
| Hair Conditioner Base | Cetyl Alcohol, Behentrimonium Chloride, *Triticum Vulgare* (Wheat) Bran Extract, Linoleic Acid | 3.00 | 3.00 |
| PCL-Solid | Stearyl Heptanoate, Stearyl Caprylate | 0.50 | 0.50 |
| Dow Corning 5200 | Laurylmethicone Copolyol | 0.50 | 0.50 |
| Natrosol 250 HR | Hydroxyethylcellulose | 0.50 | 0.50 |
| Benzophenon-4 | Benzophenone-4 | 1.00 | 0.50 |
| Neo Heliopan AP | Disodium Phenyl Dibenzimidazole Tetrasulfonate | 1.00 | 0.80 |
| Amino Methyl propanol | Amino Methyl propanol | 2.00 | 1.20 |
| Nipagin M | Methylparaben | 0.30 | 0.30 |
| Dow Corning 949 Cationic Emulsion | Amodimethicone, Cetrimonium Chloride, Trideceth-12 | 2.00 | 2.00 |
| 5-Cyclohexyl-2-methyl-pentanol of Synthesis Example 2 | | 0.35 | — |
| 5-Cyclohexyl-2-n-propyl-pentanol of Synthesis Example 1.3 | | — | 0.35 |
| Perfume oil of Example P2 | Parfum | 0.75 | — |
| Perfume oil of Example P3 | Parfum | — | 0.80 |
| Water | Water (Aqua) | To 100 | To 100 |

Example D32

Aerosol Spray

| Components | % by weight | % by weight |
|---|---|---|
| Aluminum Chlorohydrate | 30.00 | 30.00 |
| 5-Cyclohexyl-2-methyl-pentanol of Synthesis Example 2 | 0.35 | — |
| 5-Cyclohexyl-2-n-propyl-pentanol of Synthesis Example 1.3 | — | 0.30 |
| *Persea Gratissima* Oil | 0.10 | 0.10 |
| Octyldodecanol | 1.00 | 1.00 |
| Dimethicone | 3.00 | 3.00 |
| Cyclomethicone | Ad 100 | Ad 100 |
| Perfume oil of Example P2 | 4.00 | 5.00 |
| Magnesium Aluminum Silicate | 0.10 | 0.10 |
| Disteardimonium Hectorite | 4.00 | 4.00 |
| Tocopheryl Acetate | 0.10 | 0.10 |
| Butyloctanoic acid | 0.25 | 0.25 |

15 Parts of the mixture obtained by mixing together the listed components were filled with 85 parts by weight of a propane-butane mixture (propane:butane=2:7 (w/w)) into an aerosol container.

Example D33

Roll-on (Macro-Emulsion)

| Components | % by weight | % by weight |
|---|---|---|
| 3-(4-Hydroxy-3-methoxy-phenyl)-1-(4-hydroxyphenyl)-1-propanone | 0.125 | 0.125 |
| 5-Cyclohexyl-2-methyl-pentanol of Synthesis Example 2 | 0.35 | — |
| 5-Cyclohexyl-2-n-propyl-pentanol of Synthesis Example 1.3 | — | 0.30 |
| Trisodium EDTA | 1.50 | 1.50 |
| Steareth-21 | 1.50 | 1.50 |
| Steareth-2 | 2.50 | 2.50 |
| PPG-15 Stearyl Ether | 3.00 | 3.00 |
| Aluminum Chlorohydrate | 20.00 | 20.00 |
| Perfume oil of Example P3 | 1.00 | 1.00 |
| Water (Aqua) | Ad 100 | Ad 100 |

Example D34

Roll-on (Micro-Emulsion)

| Components | % by weight | % by weight |
|---|---|---|
| 5-Cyclohexyl-2-methyl-pentanol of Synthesis Example 2 | — | 0.40 |

-continued

| Components | % by weight | % by weight |
|---|---|---|
| 5-Cyclohexyl-2-n-propyl-pentanol of Synthesis Example 1.3 | 0.40 | — |
| Aluminum Chlorohydrate | 20.00 | 20.00 |
| 1,3-Butylene Glycol | 3.00 | 3.00 |
| Dicaprylyl Ether | 3.00 | 3.00 |
| Isoceteth-20 | 5.00 | 5.00 |
| Glyceryl Isostearate | 2.50 | 2.50 |
| PEG-150 Distearate | 1.00 | 1.00 |
| Perfume oil of Example P4 | 0.80 | 0.80 |
| Water (Aqua) | Ad 100 | Ad 100 |

Example D35

Deodorant Stick

| Components | % by weight | % by weight |
|---|---|---|
| 5-Cyclohexyl-2-methyl-pentanol of Synthesis Example 2 | 0.50 | — |
| 5-Cyclohexyl-2-n-propyl-pentanol of Synthesis Example 1.3 | — | 0.45 |
| Stearic Acid | 6.50 | 6.50 |
| 1,2-Propylene Glycol | 20.00 | 20.00 |
| PEG-8 | 20.00 | 20.00 |
| Ethylhexylglycerin | 0.50 | 0.50 |
| *Persea Gratissima* Oil | 0.10 | 0.10 |
| Octyldodecanol | 0.10 | 0.10 |
| Perfume oil of Example P1 | 1.00 | 1.00 |
| Water (Aqua) | Ad 100 | Ad 100 |

-continued

| Components | % by weight | % by weight |
|---|---|---|
| Butyloctanoic Acid | 0.50 | 0.50 |
| Distarch Phosphate | 0.40 | 0.40 |

Example D36

Antiperspirant Cream Deodorant for Sensitive Skin

| Components | % by weight | % by weight |
|---|---|---|
| 5-Cyclohexyl-2-methyl-pentanol of Synthesis Example 2 | 0.30 | — |
| 5-Cyclohexyl-3-n-propyl-pentanol of Synthesis Example 3 | — | 0.25 |
| Paraffinum Liquidum | 4.50 | 4.50 |
| Glyceryl Stearate | 5.00 | 5.00 |
| Water (Aqua) | ad 100 | ad 100 |
| Cetyl Alcohol | 5.00 | 5.00 |
| PEG-40 Stearate | 2.50 | 2.50 |
| Trisodium EDTA | 1.50 | 1.50 |
| *Persea Gratissima* Oil | 0.10 | 0.10 |
| C12-15 Alkyl Benzoate | 0.50 | 0.50 |
| Aluminum Chlorohydrate | 30.00 | 30.00 |
| C13-16 Isoparaffin | 4.50 | 4.50 |
| Isohexadecane | 4.50 | 4.50 |
| Caprylyl Glycol (1,2-octanediol) | 0.30 | 0.30 |
| Perfume oil of Example P4 | 0.50 | 0.50 |

Example D37

Sunscreen Spray In-Vitro SPF 20

| Part | Raw Materials | INCI Name | % (wt.) |
|---|---|---|---|
| A | Water, demin. | Water (Aqua) | Ad 100 |
|  | Glycerol, 99% | Glycerine | 4.00 |
|  | Hydrolite 5 | 1,2-Pentylene Glycol | 5.00 |
|  | D-Panthenol | Panthenol | 0.50 |
|  | Lara Care A-200 | Galactoarabinan | 0.25 |
| B | Baysilone oil M 10 | Dimethicone | 1.00 |
|  | Edeta BD | Disodium EDTA | 0.10 |
|  | Copherol 1250 | Tocopheryl Acetate | 0.50 |
|  | Cetiol OE | Dicaprylyl Ether | 3.00 |
|  | Neo Heliopan ® HMS | Homosalate | 5.00 |
|  | Neo Heliopan ® AV | Ethylhexyl Methoxycinnamate | 6.00 |
|  | Neo Heliopan ® 357 | Butyl Methoxydibenzoylmethane | 1.00 |
|  | Tinosorb ® S | Bis Ethylhexyloxyphenol Methoxyphenyl Triazine | 2.50 |
|  | Alpha-Bisabolol | Bisabolol | 0.10 |
|  | 5-Cyclohexyl-2-methyl-pentanol of Synthesis Example 2 |  | 0.30 |
|  | Pemulen TR-2 | Acrylates/C10-30 Alkyl Acrylate Crosspolymer | 0.25 |
| C | Phenoxyethanol | Phenoxyethanol | 0.70 |
|  | Solbrol M | Methylparaben | 0.20 |
|  | Solbrol P | Propylparaben | 0.10 |
|  | Neo Heliopan ® Hydro | Phenylbenzimidazole Sulfonic Acid | 2.00 |
|  | Sodium Hydroxide | Sodium Hydroxide | qs |
| D | Perfume oil of Example P2 | Fragrance (Parfum) | 0.20 |

Example D38

Sunscreen Hydrodispersion Gel (Balm)

| Part | Raw Materials | INCI Name | % (wt.) |
|---|---|---|---|
| A | Water, dist. | Water (Aqua) | Ad 100 |
|   | Carbopol Ultrez 21 | Acrylates/C10-30 Alkyl Acrylate Crosspolymer | 1.00 |
|   | Triethanolamine | Triethanolamine | 1.20 |
| B | Neo Heliopan ® AP, 22% strength solution neutralised with Triethanolamine | Disodium Phenyl Dibenzimidazole Tetrasulfonate | 10.0 |
|   | Benzophenone-4 | Benzophenone-4 | 0.5 |
|   | Triethanolamine | Triethanolamine | qs |
| C | Neo Heliopan ® E1000 | Isoamyl p-I Methoxycinnamate | 3.00 |
|   | Neo Heliopan ® 357 | Butyl Methoxydibenzoylmethane | 2.00 |
|   | Isopropyl myristate | Isopropyl Myristate | 4.00 |
|   | Baysilone oil PK 20 | Phenyl Trimethicone | 3.00 |
|   | Dragocide Liquid | Phenoxyethanol (and) Methylparaben (and) Butyparaben (and) Ethyparaben (and) Propylparaben | 0.50 |
|   | 5-Cyclohexyl-2-methyl-pentanol of Synthesis Example 2 |  | 0.30 |
|   | Perfume oil of Example P3 | Parfum (Fragrance) | 0.30 |
|   | Edeta BD | Disodium EDTA | 0.10 |
|   | Alpha Bisabolol | Alpha Bisabolol | 0.10 |

Example D39

Water Resistant Broad Spectrum O/W Emulsions
In-Vitro SPF 50+

| Part | Ingredients | INCI | A % (wt.) | B % (wt.) |
|---|---|---|---|---|
| A | Emulsiphos | Potassium Cetyl Phosphate, Hydrogenated Palm Glycerides | 3.50 | 3.50 |
|   | Lanette O | Cetearylalcohol | 1.00 | 1.00 |
|   | Neo Heliopan ® HMS | Homosalate | 5.00 | 5.00 |
|   | Neo Heliopan ® 303 | Octocrylene | 10.00 | 10.00 |
|   | Neo Heliopan ® OS | Ethylhexyl Salicylate | 5.00 | 5.00 |
|   | Neo Heliopan ® 357 | Butyl Methoxydibenzoylmethane | 5.00 | 4.50 |
|   | Eusolex T2000 | Titanium Dioxide, Alumina, Simethicone | 5.00 | 5.00 |
|   | Tinosorb S | Bis Ethylhexyloxyphenol Methoxyphenyl Triazine | 0.00 | 4.50 |
|   | Abil Wax 9801 | Cetyl Dimethicone | 1.00 | 1.00 |
|   | Silcare Silicone 41M65 | Stearyl Dimethicone | 1.00 | 1.00 |
|   | Baysilone oil PK 20 | Phenyl Trimethicone | 2.00 | 2.00 |
|   | 5-Cyclohexyl-2-methyl-pentanol of Synthesis Example 2 |  | 0.40 | — |
|   | 5-Cyclohexyl-2-n-propyl-pentanol of Synthesis Example 1.3 |  | — | 0.40 |
|   | Isoadipat | Diisopropyladipate | 2.00 | 2.00 |
|   | Tocopherylacetat | Tocopheryl Acetate | 0.50 | 0.50 |
|   | Antaron V216 | VP/Hexadecene Copolymer | 0.50 | 0.50 |
|   | EDTA BD | Disodium EDTA | 0.10 | 0.10 |
|   | Keltrol T | Xanthan Gum | 0.50 | 0.50 |
| B | Water dem | Water (Aqua) | Ad 100 | Ad 100 |
|   | Benzophenone-4 | Benzophenone-4 | 100 | 0.50 |
|   | Neo Heliopan ® AP | Disodium Phenyl Dibenzimidazole Tetrasulfonate | 2.00 | 1.50 |
|   | Phenonip | Phenoxyethanol (and) Methylparaben (and) Butyparaben (and) | 0.70 | 0.70 |

-continued

| Part | Ingredients | INCI | A % (wt.) | B % (wt.) |
|------|-------------|------|-----------|-----------|
|  |  | Ethyparaben (and) Propylparaben |  |  |
|  | Arginine | Arginine | 2.20 | 1.23 |
|  | Lara Care A-200 | Galactoarabinan | 0.25 | 0.25 |
|  | Hydrolite 5 (1,2-pentandiol) | Pentylene Glycol | 3.00 | 3.00 |
| C | Perfume oil of Example P2 | Fragrance (parfum) | 0.60 | 0.60 |

Example D40

Sunspray O/W Exp. SPF 20

| Part | Ingredients | INCI | % (wt.) |
|------|-------------|------|---------|
| A | Dracorin GOC | Glyceryl Oleate Citrate, Caprylic/Capric Triglyceride | 2.00 |
|  | Neo Heliopan HMS | Homosalate | 7.00 |
|  | Neo Heliopan 357 | Butyl Methoxydibenzoylmethane | 4.00 |
|  | Neo Heliopan OS | Ethylhexyl Salicylate | 5.00 |
|  | Isoadipat | Diisopropyl Adipate | 6.00 |
|  | Corapan TQ | Diethylhexyl 2,6 Naphthalate | 3.00 |
|  | Edeta BD | Disodium EDTA | 0.10 |
|  | Vitamin E Acetate | Tocopheryl Acetate | 0.50 |
|  | Baysilone Oil M 10 | Dimethicone | 1.00 |
|  | Alpha-Bisabolol | Bisabolol | 0.10 |
|  | Pemulen TR 2 | Acrylates/C10-30 Acrylates Copolymer | 0.25 |
|  | 5-Cyclohexyl-2-methyl-pentanol of Synthesis Example 2 |  | 0.35 |
|  | Perfume oil of Example P2 | Fragrance (parfum) | 0.20 |
| B | Deion. Wasser | Water (Aqua) | Ad 100 |
|  | Glycerin 99% | Glycerine | 4.00 |
|  | Butylenglycol | Butylene Glycol | 5.00 |
|  | Dragocid Liquid | Phenoxyethanol, Methylparaben, Ethylparaben, Butylparaben, Propylparaben, Isobutylparaben | 0.80 |
|  | Neo Heliopan ® Hydro | Phenylbenzimidazole Sulfonic Acid | 2.00 |
|  | Benzophenone-4 | Benzophenone-4 | 1.00 |
|  | Neo Heliopan ® AP | Disodium Phenyl Dibenzimidazole Tetrasulfonate | 2.00 |
|  | Tris-Hydroxyaminomethane | Tris-Hydroxyaminomethane | 0.47 |
| C | Perfume oil of Example P3 | Fragrance (parfum) | 0.40 |

Example Mint Flavor 1

Synthetic Peppermint Oil (not According to the Present Invention)

| | Aroma SP parts by weight |
|---|---|
| Isobutyraldehyde | 0.5 |
| 3-Octanol | 0.5 |
| Dimethyl sulphide | 0.5 |
| trans-2-Hexenal | 1.0 |
| cis-3-Hexenol | 1.0 |
| 4-Terpineol, natural | 1.0 |
| Isopulegol, natural | 1.0 |
| Piperitone, natural, from eucalyptus | 2.0 |
| Linalool | 3.0 |
| 8-Ocimenyl acetate, 10% in triacetin | 5.0 |
| Isoamyl alcohol | 10.0 |
| Isovaleraldehyde | 10.0 |
| alpha-Pinene, natural | 25.0 |
| beta-Pinene, natural | 25.0 |
| Neomenthol, racemic | 40.0 |
| Eucalyptol (1,8-cineol), natural | 50.0 |
| L-Menthyl acetate | 70.0 |
| L-Menthone | 220.0 |
| D-Isomenthone | 50.0 |
| L-Menthol | 484.5 |
| Total: | 1,000.00 |

Example Mint Flavor 2

Mixture Comprising Salivating Agent Trans-Pellitorin (not According to the Present Invention)

| Constituent | Proportion in wt. % |
|---|---|
| Trans-pellitorin (2E,4E-decadienoic acid-N-isobutylamide) | 0.125 |
| L-Menthane carboxylic acid N-ethylamide (WS-3, for example Millennium) | 5.00 |
| L-Menthyl lactate (Frescolat ® ML, Symrise) | 30.00 |
| O-L-Menthyl-O'-(2-hydroxyethyl) carbonate (Frescolat ® MGC, Symrise) | 10.00 |
| Peppermint oil *Mentha piperita* | 20.00 |
| Diethyl malonate | 10.00 |
| Propylene glicol | Ad 100 |

Example OC1

Transparent Tooth Gel with Capsules

| Ingredients | I (wt. %) | II (wt. %) | III (wt. %) |
|---|---|---|---|
| Sorbitol, 70% strength | Ad 100 | Ad 100 | Ad 100 |
| Distilled water | 11.40 | 11.40 | 11.40 |
| Saccharin | 0.20 | 0.20 | 0.20 |
| Sodium monofluorophosphate | 1.10 | 1.10 | 1.10 |
| Trisodium phosphate | 0.10 | 0.10 | 0.10 |
| Polyethylene glycol PEG 1500 (PEG-32) | 5.50 | 5.50 | 5.50 |
| Abrasive silica gel | 8.00 | 8.00 | 8.00 |
| Thickening silica gel | 8.00 | 8.00 | 8.00 |
| Sodium carboxymethyl cellulose | 0.60 | 0.60 | 0.60 |
| Sodium lauryl sulphate | 1.50 | 1.50 | 1.50 |
| Example Mint Flavor 1 | 0.80 | 1.10 | 0.90 |
| Example Mint Flavor 2 | — | — | 0.10 |
| 5-Cyclohexyl-2-methyl-pentanol of Synthesis Example 2 | 0.60 | 0.45 | — |
| 5-Cyclohexyl-2-n-propyl-pentanol of Synthesis Example 1.3 | — | — | 0.50 |
| Blue and red colored microcapsules | 0.50 | 0.80 | 0.70 |
| 4-Hydroxybenzoic acid methylester | 0.10 | 0.10 | 0.10 |

Example OC2

Calcium Carbonate Based Toothpaste (pH=9.6)

| Ingredients | Wt. % | Wt. % | Wt. % |
|---|---|---|---|
| Calcium carbonate | 40.00 | 40.00 | 40.00 |
| Sorbitol | 27.00 | 27.00 | 27.00 |
| Hydrated silica | 2.00 | 2.00 | 2.00 |
| Sodium monofluorophosphate | 0.80 | 0.80 | 0.80 |
| Trisodium phosphate | 0.50 | 0.50 | 0.50 |
| Titanium dioxide | 1.00 | 1.00 | 1.00 |
| Sodium carboxymethyl cellulose | 0.90 | 0.90 | 0.90 |
| Sodium lauryl sulphate | 2.00 | 2.00 | 2.00 |
| Sodium saccharin | 0.20 | 0.20 | 0.20 |
| Sodium fluoride | 0.20 | 0.20 | 0.20 |
| Example Mint Flavor 1 | 1.00 | 1.10 | 1.00 |
| Example Mint Flavor 2 | — | 0.20 | — |
| 5-Cyclohexyl-2-methyl-pentanol of Synthesis Example 2 | 0.50 | — | — |
| 5-Cyclohexyl-2-n-propyl-pentanol of Synthesis Example 1.3 | — | — | 0.60 |
| Water | Ad 100 | Ad 100 | Ad 100 |

Example OC3

Ready-to-Use Mouthwash Composition

| Ingredients | Wt. % | Wt. % |
|---|---|---|
| Ethanol | 7.00 | 7.00 |
| Glycerin | 12.00 | 12.00 |
| Sodium fluoride | 0.05 | 0.05 |
| Pluronic F-127 ® (BASF, surfactant) | 1.40 | 1.40 |
| Na-phosphate buffer pH 7.0 | 1.10 | 1.10 |
| Sorbic acid | 0.20 | 0.20 |
| Sodium saccharin | 0.10 | 0.10 |
| Example Mint Flavor 1 | 0.40 | 0.30 |
| Example Mint Flavor 2 | — | 0.10 |
| 5-Cyclohexyl-2-methyl-pentanol of Synthesis Example 2 | 0.30 | — |
| 5-Cyclohexyl-3-methyl-pentanol of Synthesis Example 3 | — | 0.30 |
| 2-(Benzylamino)benzoic acid | 0.25 | 0.25 |
| Color FD&C Blue #1 | 0.01 | 0.01 |
| Water | Ad 100 | Ad 100 |

Example OC4

Gel Dental Cream

| | I (wt. %) | II (wt. %) | III (wt. %) |
|---|---|---|---|
| Na-carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na-saccharinate | 0.07 | 0.07 | 0.07 |
| Na-fluoride | 0.24 | 0.24 | 0.24 |
| p-Hydroxybenzoic acid (PHB) ethyl ester | 0.15 | 0.15 | 0.15 |
| Abrasive silica | 11.00 | 11.00 | 11.00 |
| Thickening silica | 6.00 | 6.00 | 6.00 |
| Triclosan (2,4,4'-tri-chlor-2'-hydroxydiphenyl ether) | — | 0.30 | 0.30 |
| Example Mint Flavor 1 | 0.80 | 1.00 | 1.00 |
| Example Mint Flavor 2 | 0.20 | — | — |

-continued

|  | I (wt. %) | II (wt. %) | III (wt. %) |
|---|---|---|---|
| 5-Cyclohexyl-2-methyl-pentanol of Synthesis Example 2 | 0.40 | 0.30 | — |
| 5-Cyclohexyl-2-n-propyl-pentanol of Synthesis Example 1.3 | — | — | 0.40 |
| Menthone glycerine acetal (Frescolat ® MGA) | — | 0.10 | 0.10 |
| Sodium dodecyl sulfate (SDS) | 1.40 | 1.40 | 1.40 |
| Dist. water | Ad 100.00 | Ad 100.00 | Ad 100.00 |

Example OC5

Dental Cream

|  | I (wt. %) | II (wt. %) | III (wt. %) |
|---|---|---|---|
| Carrageenan | 0.90 | 0.90 | 0.90 |
| Glycerol | 15.00 | 15.00 | 15.00 |
| Sorbitol 70%, in water | 25.00 | 25.00 | 25.00 |
| PEG 1000 | 3.00 | 3.00 | 3.00 |
| Na-fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccarinate | 0.40 | 0.40 | 0.40 |
| Precipitated silica | 20.00 | 20.00 | 20.00 |
| Titanium dioxide | 1.00 | 1.00 | 1.00 |
| p-Hydroxybenzoic acid methyl ester | 0.10 | 0.10 | 0.10 |
| Example Mint Flavor 1 | 0.60 | 1.00 | 1.25 |
| Example Mint Flavor 2 | 0.50 | 0.10 | — |
| 5-Cyclohexyl-2-methyl-pentanol of Synthesis Example 2 | 0.45 | 0.30 | — |
| 5-Cyclohexyl-2-n-propyl-pentanol of Synthesis Example 1.3 | — | 0.20 | 0.50 |
| 2-(Benzylamino)benzoic acid | 0.30 | — | 0.30 |
| Sodium dodecyl sulfate | 1.30 | 1.30 | 1.30 |
| Dist. Water | Ad 100.00 | Ad 100.00 | Ad 100.00 |

Example OC6

Dental Cream Against Sensitive Teeth

|  | I (wt. %) | II (wt. %) | III (wt. %) |
|---|---|---|---|
| Na-carboxymethylcellulose | 0.70 | 0.70 | 0.70 |
| Xanthan Gum | 0.50 | 0.50 | 0.50 |
| Glycerol | 15.00 | 15.00 | 15.00 |
| Sorbitol 70%, in water | 12.00 | 12.00 | 12.00 |
| K-nitrate | 5.00 | 5.00 | 5.00 |
| Na-monofluorophosphate | 0.80 | 0.80 | 0.80 |
| p-Hydroxybenzoic acid methyl ester | 0.15 | 0.15 | 0.15 |
| p-Hydroxybenzoic acid propyl ester | 0.05 | 0.05 | 0.05 |
| Na saccharinate | 0.20 | 0.20 | 0.20 |
| Wintergreen flavor (contains methyl salicylate) | 0.80 | 0.70 | 0.60 |
| Example Mint Flavor 2 | 0.20 | 0.40 | 0.50 |
| 5-Cyclohexyl-2-methyl-pentanol of Synthesis Example 2 | 0.40 | 0.30 | — |
| 5-Cyclohexyl-2-n-propyl-pentanol of Synthesis Example 1.3 | — | 0.20 | 0.50 |
| Ca-carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Dist. Water | Ad 100.00 | Ad 100.00 | Ad 100.00 |

Example OC7

Mouthwash Concentrate

|  | I (wt. %) | II (wt. %) | III (wt. %) |
|---|---|---|---|
| Ethanol, 95% strength | 80.00 | 80.00 | 80.00 |
| Na cyclamate | 0.15 | 0.15 | 0.15 |
| Eucalyptol flavor (contains 74 wt. % natural eucalyptol) | 1.50 | 1.00 | 2.00 |
| Dyestuff | 0.01 | 0.01 | 0.01 |
| Example Mint Flavor 1 | 0.75 | 1.00 | — |
| Example Mint Flavor 2 | 0.10 | — | 0.15 |
| 5-Cyclohexyl-2-methyl-pentanol of Synthesis Example 2 | — | 1.20 | 2.00 |
| 5-Cyclohexyl-2-n-propyl-pentanol of Synthesis Example 1.3 | 1.00 | — | — |
| Dist. water | Ad 100.00 | Ad 100.00 | Ad 100.00 |

Example OC8a-8c

Sugar-Free Chewing Gums

Example OC8a

Non-Stick Chewing Gum

Chewing gum base K1 comprised 2.0% butyl rubber (isobutene/isoprene copolymer, MW 400,000), 6.0% polyisobutene (MW=43,800), 43.5% polyvinyl acetate (MW 12,000), 31.5% polyvinyl acetate (MW=47,000), 6.75% triacetin and 10.25% calcium carbonate. Chewing gum base K1 and the chewing gums can be prepared analogously to U.S. Pat. No. 5,601,858.

|  | I (wt. %) | II (wt. %) | III (wt. %) |
|---|---|---|---|
| Chewing gum base K1 | 26.00 | 26.00 | 26.00 |
| Triacetin | 0.25 | 0.25 | 0.25 |
| Lecithin | 0.50 | 0.50 | 0.50 |
| Sorbitol, cristalline | Ad 100 | Ad 100 | Ad 100 |
| Mannitol | 15.30 | 15.20 | 15.10 |
| Glycerol | 12.10 | 12.00 | 11.80 |
| Aspartame | 0.17 | 0.17 | 0.17 |
| Encapsulated aspartame | 1.08 | 1.08 | 1.08 |
| Amorphous silica | 1.00 | 1.00 | 1.00 |
| Cottonseed oil | 0.50 | 0.50 | 0.50 |
| Polyoxyethylene sorbitan monolaurate (E-432) | 1.00 | 1.00 | 1.00 |
| Menthone glycerine acetal (Frescolat ® MGA) | — | 0.15 | — |
| Encapsulated spearmint flavor (contains 55 wt. % l-carvone) | 0.20 | 0.10 | 0.35 |

-continued

|  | I (wt. %) | II (wt. %) | III (wt. %) |
|---|---|---|---|
| Encapsulated wintergreen flavor (contains methyl salicylate) | — | 0.10 | — |
| Example Mint Flavor 1 | 1.30 | 1.10 | 1.50 |
| Example Mint Flavor 2 | 0.10 | 0.30 | — |
| 5-Cyclohexyl-2-methyl-pentanol of Synthesis Example 2 | 0.60 | 0.40 | 0.50 |

Example OC8b

Chewing gum base K2 comprised 28.5% terpene resin, 33.9% polyvinyl acetate (MW=14,000), 16.25% hydrogenated plant oil, 5.5% mono- and diglycerides, 0.5% polyisobutene (MW 75,000), 2.0% butyl rubber (isobutene/isoprene copolymer), 4.6% amorphous silicon dioxide (water content approx. 2.5%), 0.05% antioxidant tert-butylhydroxytoluene (BHT), 0.2% lecithin, and 8.5% calcium carbonate. Chewing gum base K2 and the chewing gums can be prepared analogously to U.S. Pat. No. 6,986,907.

|  | I (wt. %) | II (wt. %) | III (wt. %) |
|---|---|---|---|
| Chewing gum base K2 | 25.30 | 27.30 | 26.30 |
| Sorbitol | Ad 100 | Ad 100 | Ad 100 |
| Glycerol | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.68 |
| Menthol, spray-dried | 0.25 | 0.10 | 0.50 |
| Lemon aroma, spray-dried | — | 1.20 | — |
| Example Mint Flavor 1 | 1.30 | 0.70 | 1.50 |
| Example Mint Flavor 2 | 0.10 | 0.15 | — |
| 5-Cyclohexyl-2-methyl-pentanol of Synthesis Example 2 | 0.50 | 0.70 | — |
| 5-Cyclohexyl-3-methyl-pentanol of Synthesis Example 3 | — | — | 0.60 |

The chewing gums of recipe (I) and (II) were shaped as strips, and those of recipe (III) were shaped as pellets.

Example OC8c

|  | I (wt. %) | II (wt. %) | III (wt. %) |
|---|---|---|---|
| Chewing gum base | 30.00 | 30.00 | 30.00 |
| Sorbitol, powder | Ad 100 | Ad 100 | Ad 100 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerol | 1.00 | 1.00 | 1.00 |
| 2-(Benzylamino)benzoic acid | 0.35 | 0.45 | — |
| Example Mint Flavor 1 | 1.50 | 1.20 | 1.25 |
| Example Mint Flavor 2 | — | 0.20 | — |
| 5-Cyclohexyl-2-methyl-pentanol of Synthesis Example 2 | 0.60 | — | 0.35 |
| 5-Cyclohexyl-2-n-propyl-pentanol of Synthesis Example 1.3 | — | 0.75 | 0.40 |

Example OC9

Gelatine Capsule

|  | I (wt. %) | II (wt. %) | III (wt. %) |
|---|---|---|---|
| Gelatine shell: | | | |
| Glycerol | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core composition: | | | |
| Plant oil triglyceride (coconut oil fraction) | 81.28 | 66.05 | 60.10 |
| Flavor DC* | 16.00 | 30.0 | 24.50 |
| 5-Cyclohexyl-2-methyl-pentanol of Synthesis Example 2 | 1.50 | 3.00 | — |
| 5-Cyclohexyl-2-n-propyl-pentanol of Synthesis Example 1.3 | — | — | 4.00 |
| Sucralose | 0.22 | 0.30 | 0.70 |
| Example Mint Flavor 1 | — | — | 10.00 |
| Example Mint Flavor 2 | 1.00 | — | — |
| (1R,3R,4S) Menthyl-3-carboxylic acid N-ethylamide (WS-3) | — | 0.35 | 0.10 |
| (−)-Menthone glycerol acetal (Frescolat ® MGA) | — | 0.30 | 0.60 |

*Flavor DC had the following composition (figures in wt. %): 0.1% neotame powder, 0.05% aspartame, 29.3% peppermint oil *arvensis*, 29.3% peppermint *piperita* oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, was prepared in accordance with WO 2004/050069 and had a diameter of 5 mm, and the weight ratio of core material to shell material was 90:10. The capsules opened in the mouth within less than 10 seconds and dissolved completely within less than 50 seconds.

Example OC10

Throat Candies with a Liquid-Viscous Core Filling (Centre-Filled Hard Candy)

|  | I (wt. %) | II (wt. %) |
|---|---|---|
| Part A (shell) (80% of the candy) | | |
| Sugar (sucrose) | Ad 100 | Ad 100 |
| Glucose syrup (solids content 80%) | 41.51 | 49.37 |
| Example Mint Flavor 1 | 0.75 | 0.75 |
| 5-Cyclohexyl-2-methyl-pentanol of Synthesis Example 2 | 0.25 | 0.40 |

-continued

|  | I (wt. %) | II (wt. %) |
| --- | --- | --- |
| Lemon oil | 0.10 | 0.10 |
| Citric acid | — | 0.91 |
| Total A: | 100 | 100 |
| Part B (core) (20% of the candy) | | |
| High fructose corn syrup (content of solid sugars 85%, close to 15% water) | Ad 100 | Ad 100 |
| Glycerol | 15.0 | 15.0 |
| Lecithin | 0.02 | 0.02 |
| Cinnamon oil | — | 0.32 |
| Example Mint Flavor 2 | 0.20 | — |
| Capsaicin | 0.05 | — |
| Vanillyl alcohol n-butyl ether | — | 0.10 |
| Red dyestuff, as a 5% strength aqueous solution | 0.20 | 0.20 |
| Vanillin | 0.07 | — |
| Total B: | 100 | 100 |

Candies having a liquid-viscous core were prepared in accordance with the processes described in U.S. Pat. No. 6,432,441 (Example 1 there) and in U.S. Pat. No. 5,458,894 and U.S. Pat. No. 5,002,791. The two parts A and B were processed separately to bases for the shell (Part A) and core (Part B). The filled throat candies obtained by means of co-extrusion acted against coughing, sore throat and hoarseness when consumed by affected persons.

Example OC11

Dental Cream and Mouthwash as a 2-in-1 Product

|  | I (wt. %) | II (wt. %) |
| --- | --- | --- |
| Sorbitol | 40.00 | 45.00 |
| Glycerin | 20.00 | 20.00 |
| Ethanol | 5.00 | — |
| Water | Ad 100 | Ad 100 |
| Solbrol M, Na-salt (Methylparaben, sodium salt) | 0.15 | 0.15 |
| Na-monofluorphosphate | 0.75 | 0.75 |
| Saccharine | 0.20 | 0.20 |
| Abrasive silica (Sident 9, Degussa) | 20.00 | 20.00 |
| Thickening silica (Sident 22, Degussa) | 2.00 | 2.00 |
| Sodium carboxymethyl cellulose | 0.30 | 0.30 |
| Sodium lauryl sulfate (SLS) | 1.20 | 1.20 |
| Color (1% in water) | 0.50 | 0.50 |
| 5-Cyclohexyl-2-methyl-pentanol of Synthesis Example 2 | 0.60 | 0.90 |
| Example Mint Flavor 1 | 1.00 | 1.25 |
| Example Mint Flavor 2 | 0.15 | — |

Example OC12

Toothpaste with Bleaching Activity

|  | I (wt.-%) | II (wt.-%) | II (wt.-%) |
| --- | --- | --- | --- |
| Polyphosphate (Glass H, (n ≈ 21), Astaris) | 7.00 | 7.00 | 7.00 |
| Ca-peroxide | 1.00 | — | 2.50 |
| Na-percarbonate | — | 11.00 | — |
| Poloxamer 407 | 5.00 | 2.00 | 5.00 |
| Polyethylenglycol | 3.00 | — | 3.00 |
| Sorbitol, 70% in water | — | 22.00 | — |
| Glycerine | 43.80 | 12.50 | 28.60 |
| 1,2-Propyleneglycol | 4.00 | — | 2.50 |
| Na-Saccharin | 0.40 | 0.20 | 0.50 |
| Na-bicarbonate | — | 5.00 | 15.00 |
| Na-carbonate | 2.00 | 2.00 | 2.00 |
| Silica | 20.00 | 22.00 | 20.00 |
| Na-Carboxymethyl cellulose | 0.60 | 0.55 | 0.30 |
| Na-lauryl sulfate | 1.00 | 4.00 | 2.00 |
| Xanthan Gum | 0.20 | 0.20 | 0.20 |
| Titanium dioxide (Anatas) | 0.50 | 0.50 | 0.50 |
| Example Mint Flavor 1 | 1.00 | 1.25 | 1.00 |
| Example Mint Flavor 2 | — | — | 0.25 |
| 5-Cyclohexyl-2-methyl-pentanol of Synthesis Example 2 | 0.35 | — | 0.50 |
| 5-Cyclohexyl-2-n-propyl-pentanol of Synthesis Example 1.3 | — | 0.30 | — |
| Water | Ad 100 | Ad 100 | Ad 100 |

Example OC13

Toothpaste with Tin and Zinc Salts

|  | I (wt.-%) | II (wt.-%) | II (wt.-%) |
| --- | --- | --- | --- |
| NaF | 0.42 | 0.50 | — |
| Sn-fluoride $SnF_2$ | — | 0.90 | 0.95 |
| Sn-chloride $SnCl_2$ | 1.50 | — | 2.00 |
| Zinc-lactate | 2.00 | 2.00 | — |
| Zn-carbonate $ZnCO_3$ | — | 1.00 | 1.50 |
| Na-gluconate | — | 0.67 | 1.50 |
| Poloxamer 407 | 14.50 | — | — |
| Polyethylenglycol | 1.00 | 3.00 | — |
| Sorbitol, 70% in water | — | 38.00 | 37.50 |
| Glycerine | 37.50 | 5.00 | 14.40 |
| 1,2-Propylene glycol | 7.00 | 5.00 | — |
| Na-saccharin | 0.30 | 0.50 | 0.50 |
| Abrasive silica | 20.00 | 22.50 | 25.00 |
| NaOH | — | 0.10 | 0.20 |
| Na-lauryl sulfate | — | 2.00 | 1.50 |
| Na-polyphosphate | — | — | 4.00 |
| Tetra-Na-pyrophosphate | 1.00 | 2.50 | — |
| Colorant (1% in water) | 0.40 | 0.50 | 0.50 |
| Example Mint Flavor 1 | 0.85 | 1.25 | 1.50 |
| Example Mint Flavor 2 | 0.15 | 0.10 | — |
| 5-Cyclohexyl-2-methyl-pentanol of Synthesis Example 2 | 0.50 | — | 0.25 |
| 5-Cyclohexyl-2-n-propyl-pentanol of Synthesis Example 1.3 | — | 0.40 | 0.25 |
| Water | Ad 100 | Ad 100 | Ad 100 |

The invention claimed is:
1. A compound of the formula

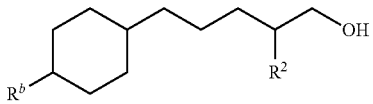 (IV)

wherein
R² denotes a linear or branched alkyl radical having 1 to 6 carbon atoms, and $R^b$ denotes hydrogen, methyl, ethyl, propyl, isopropyl or tert.-butyl.

2. An antimicrobially active cosmetic formulation or an antimicrobially active pharmaceutical formulation comprising a compound as claimed in claim 1.

3. A method for producing a compound as claimed in claim 1 comprising:
reducing a ω-phenylalkan-1-ole of formula (S) in the presence of a hydrogenation catalyst

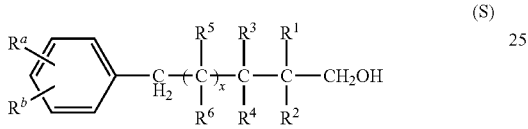 (S)

wherein $R^1$, $R^3$ to $R^6$, and $R^a$ denote hydrogen,
$R^2$ and $R^b$ have the corresponding meaning given in claim 1, and
x is 1.

4. The method of claim 3, wherein the hydrogenation catalyst comprises ruthenium, rhodium, iridium, nickel, palladium and/or platinum.

5. A composition comprising:
(a) an antimicrobially active amount of one or more compounds according to claim 1, and
(b) a carrier substance compatible with component (a) amount of one or more compounds according to claim 1.

6. The composition according to claim 5, wherein the composition is a topical cosmetic formulation, a pharmaceutical formulation or an oral hygiene product.

7. The cosmetic formulation according to claim 6, further comprising a perfume oil in the range of 0.1 to 3 wt.-%, relative to the total mass of the formulation.

8. The cosmetic formulation according to claim 6, further comprising a perfume oil in the range of 0.2 to 2 wt.-%, relative to the total mass of the formulation.

9. The cosmetic formulation according to claim 6, wherein the total to 10 wt.-% relative to the total mass of the formulation.

10. The cosmetic formulation of claim 6, wherein the cosmetic formulation is in an application form selected from the group consisting of a stick, a cream, a gel, a lotion, a foam, a roll-on preparation, a powder spray, an aerosol and a non-aerosol spray.

11. The cosmetic formulation of claim 6, wherein the formulation is a deodorant or an antiperspirant.

12. A fragrance composition comprising:
(a) an antimicrobially active amount of the one or more compounds according to claim 1;
(b) an active amount of a fragrance; and
(c) optionally one or more carriers and/or additives.

13. A method
for reducing the growth rate of *Corynebacterium xerosis* and/or *Staphylococcus epidermidis* and/or *Brevibacterium epidermidis*,
or reducing body odor, or
for inhibiting or preventing the growth of a biofilm or for reducing a biofilm, comprising topically administering a compound according to claim 1 to a human body.

14. A method
for reducing the growth rate of *Corynebacterium xerosis* and/or *Staphylococcus epidermidis* and/or *Brevibacterium epidermidis*,
for reducing body odor, or
for inhibiting or preventing the growth of a biofilm or for reducing a biofilm, comprising topically administering a composition according to claim 5 to a human body.

* * * * *